(12) United States Patent
Hosaka et al.

(10) Patent No.: US 8,435,173 B2
(45) Date of Patent: *May 7, 2013

(54) ENDOSCOPE

(75) Inventors: Yoichi Hosaka, Iruma (JP); Takakazu Ishigami, Tama (JP); Yasunda Tanaka, Hino (JP)

(73) Assignee: Olympus Corporation, Tokyo (JP)

( * ) Notice: Subject to any disclaimer, the term of this patent is extended or adjusted under 35 U.S.C. 154(b) by 1258 days.

This patent is subject to a terminal disclaimer.

(21) Appl. No.: 12/177,576

(22) Filed: Jul. 22, 2008

(65) Prior Publication Data
US 2008/0300457 A1 Dec. 4, 2008

Related U.S. Application Data

(63) Continuation-in-part of application No. 11/398,543, filed on Apr. 6, 2006, now Pat. No. 8,308,637, which is a continuation of application No. PCT/JP2004/014617, filed on Oct. 4, 2004.

(30) Foreign Application Priority Data

Oct. 6, 2003 (JP) .................................. 2003-347645
Jul. 23, 2007 (JP) .................................. 2007-190674

(51) Int. Cl.
*A61B 1/06* (2006.01)
(52) U.S. Cl.
USPC .......................................................... 600/178
(58) Field of Classification Search .................. 600/172, 600/180, 175–178
See application file for complete search history.

(56) References Cited

U.S. PATENT DOCUMENTS

| | | | |
|---|---|---|---|
| 4,301,790 A | 11/1981 | Bol et al. | |
| 4,860,732 A | 8/1989 | Hasegawa et al. | |
| 5,531,664 A | 7/1996 | Adachi et al. | |
| 6,095,970 A | 8/2000 | Hidaka et al. | |
| 6,449,006 B1 | 9/2002 | Shipp | |
| 6,796,939 B1 | 9/2004 | Hirata et al. | |
| 2003/0035048 A1 | 2/2003 | Shipp | |
| 2004/0199052 A1 | 10/2004 | Banik et al. | |

FOREIGN PATENT DOCUMENTS

| | | |
|---|---|---|
| JP | 53-43989 | 4/1978 |
| JP | 59-175194 | 10/1984 |
| JP | 60-72528 | 4/1985 |
| JP | 02-160211 | 6/1990 |
| JP | 08-104026 | 4/1996 |
| JP | 10-229966 | 9/1998 |
| JP | 11-216113 | 8/1999 |
| JP | 11-267099 | 10/1999 |
| JP | 2000-089130 A | 3/2000 |

(Continued)

*Primary Examiner* — Philip R Smith
(74) *Attorney, Agent, or Firm* — Dickstein Shapiro LLP

(57) ABSTRACT

An endoscope is provided capable of performing excellent observation for a long time by preventing decrease in light amount and generation of image noise caused by heat generated by an LED illumination even in a case where a distal-end adapter configured of the LED illumination is arranged at the distal end portion of the insertion unit. One end portion of a heat-radiating member configured of a plurality of elongated wires is arranged in the vicinity of a light emitting device, on the other hand, the other end portion of the heat-radiating member is arranged at a predetermined position on a proximal end side of an insertion unit, and a binding member for binding the wires of the heat-radiating member is provided on a side in the vicinity of the light emitting device of the heat-radiating member.

17 Claims, 38 Drawing Sheets

FOREIGN PATENT DOCUMENTS

| | | |
|---|---|---|
| JP | 2001-037712 | 2/2001 |
| JP | 2001-061777 | 3/2001 |
| JP | 2002-000562 | 1/2002 |
| JP | 2002-51971 | 2/2002 |
| JP | 2002-177197 | 6/2002 |
| JP | 2002-224015 | 8/2002 |
| JP | 2003-024276 | 1/2003 |

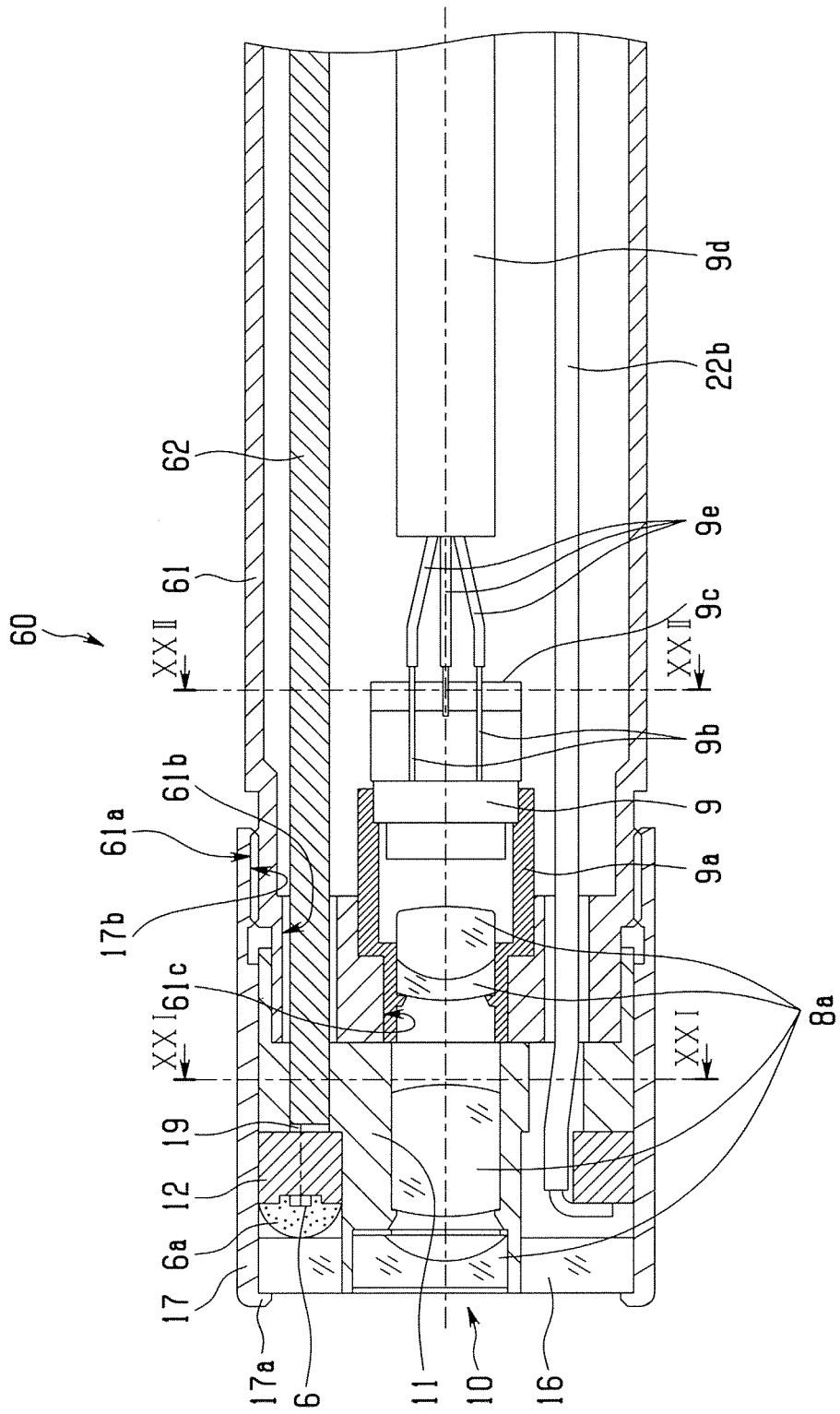

ENDOSCOPE

CROSS REFERENCES TO RELATED APPLICATIONS

This application is a continuation-in-part of U.S. application Ser. No. 11/398,543 filed on Apr. 6, 2006 which is a continuation application of PCT/JP2004/014617 filed on Oct. 4, 2004 and claims benefit of Japanese Applications No. 2007-190674 filed in Japan on Jul. 23, 2007 and No. 2003-347645 filed in Japan on Oct. 6, 2003, the entire contents of which are incorporated herein by this reference.

BACKGROUND OF THE INVENTION

1. Field of the Invention

The present invention relates to an endoscope using light emitting devices, serving as an illumination optical system, and an endoscope to which an adapter using light emitting devices serving as an illumination optical system is attachable.

2. Description of the Related Art

Endoscopes are widely used in the medical and industrial fields. Objects to be inspected using endoscopes are in living bodies and plants. Therefore, each endoscope requires a light source for illuminating an observation object.

General endoscope apparatuses each provide a light source, serving as an external device for an endoscope. Illumination rays emitted from the light source are supplied to a light guide disposed in the endoscope. The supplied illumination rays are transmitted through the light guide and are then emitted from an illumination window arranged at the distal end of an insertion unit, thus illuminating an observation area.

A recently proposed endoscope has an LED illumination system at the distal end of its insertion unit instead of the combination of a light source for illuminating an observation area and a light guide fiber. According to this endoscope, an observation area is directly illuminated by light emitted from the LED illumination system. In addition, the endoscope captures, using a solid-state image pickup device, an image of an observation area illuminated by light emitted from the LED illumination system. The above-described technique realizes a high functional endoscope having a small-diameter insertion unit and a simple structure.

Japanese Unexamined Patent Application Publication No. 2002-51971 discloses an endoscope in which the amount of illumination rays of an LED illumination system is increased, the system being arranged at the distal end of an insertion unit.

According to a known technique, to observe an observation area illuminated by illumination rays or the like using an endoscope, an adapter for changing optical characteristics, such as the direction of view and the angle of view, depending on the purpose of observation, is attached to the distal end of an insertion unit of the endoscope. In other words, a distal-end adapter is attached to the distal end of the insertion unit, thus achieving various observations using one endoscope. Therefore, when the above-described LED illumination system is arranged to the adapter, the usability of the endoscope can be improved.

SUMMARY OF THE INVENTION

According to the present invention, there is provided an endoscope including: light emitting devices arranged in its distal end portion; and at least one elongated heat-radiating member, one end of the member being arranged in the vicinity of the light emitting devices, the other end being arranged in a predetermined position adjacent to the proximal end of the insertion unit.

According to the present invention, there is provided an endoscope specifically including: a distal-end adapter including light emitting devices constituting an illumination optical system, a substrate for the light emitting devices, a support member for supporting the substrate, a first heat-conducting member through which heat generated by the light emitting devices is conducted, and an objective optical system constituting an observation optical system, the light emitting devices being arranged in one surface of the distal-end adapter, the substrate having a first electric connecting unit for the light emitting devices which is arranged in the other surface of the distal-end adapter; and an insertion unit having a distal end portion from which the distal-end adapter is detachable, the distal end portion including an image pickup device constituting the observation optical system, a second electric connecting unit which is electrically connected to the first electric connecting unit in the substrate, a second heat-conducting member through which the heat transferred through the first heat-conducting member is further conducted, and a heat-radiating member for radiating the heat conducted through the second heat-conducting member from the distal end portion in the direction toward the proximal end of the endoscope.

BRIEF DESCRIPTION OF THE DRAWINGS

FIG. 20 is a sectional view at the line XX-XX of FIG. 19;

DESCRIPTION OF THE PREFERRED EMBODIMENTS

Embodiments of the present invention will be described below with reference to the drawings.

A first embodiment of the present invention will now be described with reference to FIGS. 1 to 14.

Figure 2:
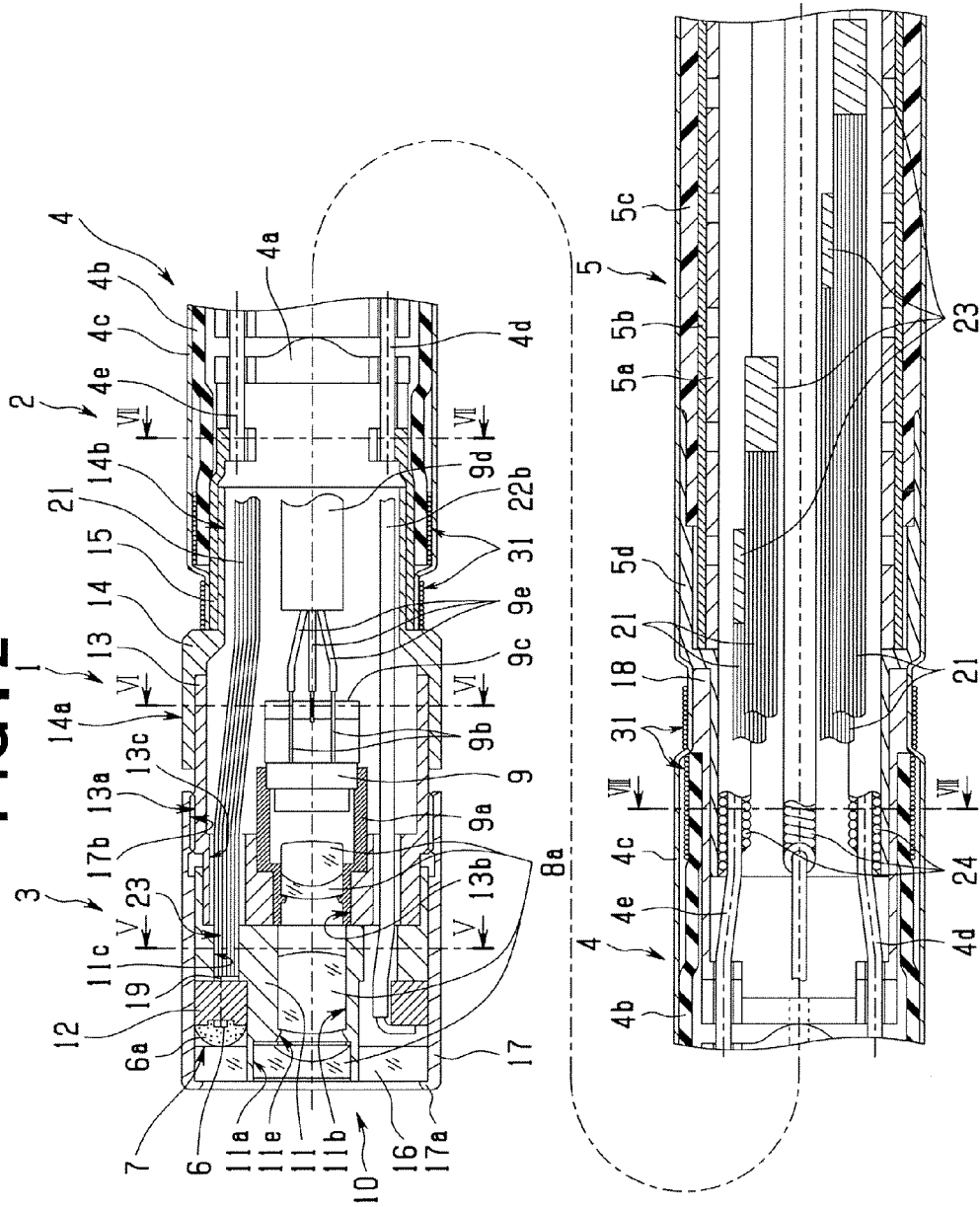
FIG. 2 is a sectional view at the line II-II of FIG. 1.

As shown in FIG. 2, an endoscope 1 according to the present embodiment has an elongated insertion unit 2. The insertion unit 2 includes a rigid distal end portion 3, a bending portion 4, and a flexible tube 5 which are connected in that order viewing from the distal end of the endoscope 1. The bending portion 4 includes a plurality of pieces connected to each other so that the portion 4 is bendable in the lateral and longitudinal directions. The flexible tube 5 is made of a flexible tubular member.

The distal end portion 3 has an LED illumination unit 7 and an observation optical unit 10. The LED illumination unit 7 includes a plurality of light emitting devices, such as light-emitting diode (LED) chips 6. The observation optical unit 10 includes a plurality of optical lenses 8a and a charge coupled device (CCD) 9.

The distal end portion 3 includes an objective optical system holder (hereinafter, abbreviated to the objective holder) 11, an LED substrate 12 for light emitting devices, a lens frame holder 13, a first connecting tube 14, a second connecting tube 15, a cover glass 16, and a connection fixing member 17.

Each of the objective holder 11 and the LED substrate 12 is made of a metal having a high thermal conductivity, such as copper or aluminum. On the other hand, each of the first connecting tube 14, the second connecting tube 15, and the connection fixing member 17, serving as the exteriors of the lens frame holder 13 and the endoscope 1, is made of a highly corrosion resistant metal having a low thermal conductivity, such as stainless steel.

Some of the optical lenses 8a, constituting the observation optical unit 10, are fixed in the objective holder 11 and the other optical lenses 8a and the CCD 9 are fixed in a lens frame 9a. Terminals 9b extending from the CCD 9 toward the proximal end of the endoscope 1 are electrically connected to a CCD substrate 9c. Signal lines 9e, passing through a signal cable 9d, are electrically connected to predetermined portions in the CCD substrate 9c.

The lens frame 9a is made of a highly corrosion resistant metal having a low thermal conductivity, such as stainless steel.

Figure 3:
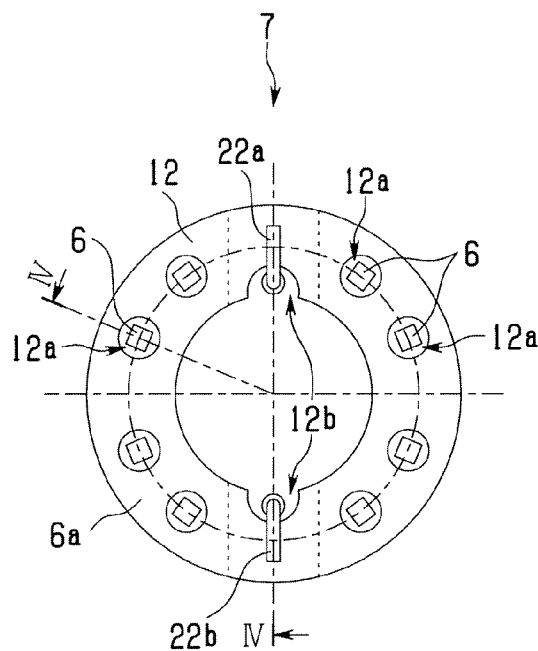
FIG. 3 is a diagram explaining an example of the arrangement of LED chips on an LED substrate.
Figure 4:
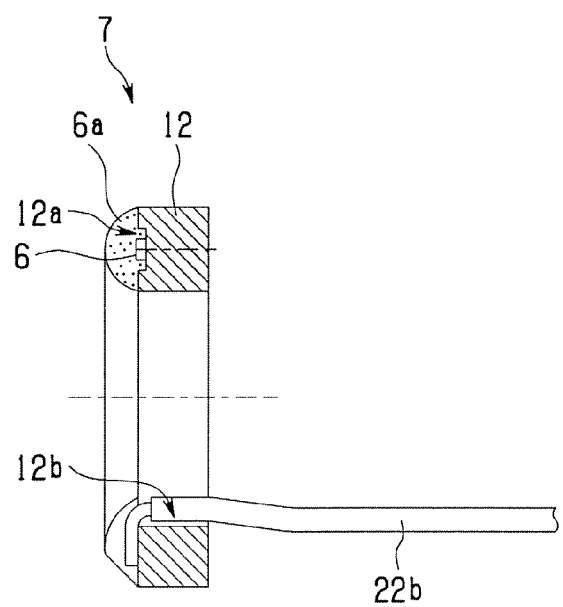
FIG. 4 is a sectional view at the line IV-IV of FIG. 3.

Referring to FIGS. 2 to 4, the LED illumination unit 7 includes the LED chips 6 and the LED substrate 12. The LED substrate 12 is ring-shaped and has, e.g., eight counterbored holes 12a which are formed at regular intervals at a predetermined distance from the center of the ring. The LED chips 6 are disposed in the counterbored holes 12a, respectively. Each LED chip 6 in the radiation direction is covered with a translucent sealing compound 6a.

A pair of notches 12b is formed on the inner surface of the LED substrate 12 so as to accommodate power cables 22a and 22b for power supply. In addition, the LED substrate 12 has a conductive pattern (not shown) that electric contacts (not shown) of the power cables 22a and 22b and the LED chips 6 are in electric contact with.

Figure 5:
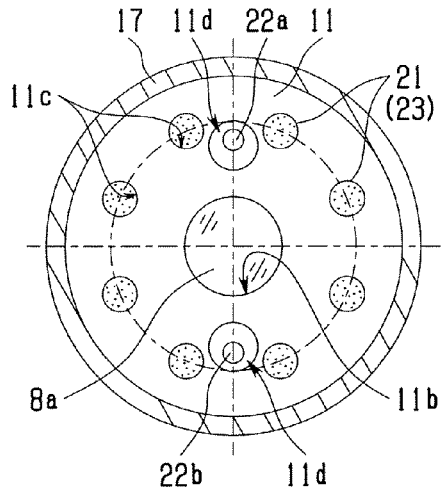
FIG. 5 is a sectional view at the line V-V of FIG. 2.

Referring to FIGS. 2 and 5, the objective holder 11 is substantially cylindrical. On the inner surface of the objective holder 11, recesses 11a and 11b are formed to accommodate the optical lenses 8a of the observation optical unit 10. The recess 11a is adjacent to the distal end of the objective holder 11 and the other recess 11b is adjacent to the proximal end thereof.

Heat-radiating member accommodation holes 11c are formed around the recess 11b at regular intervals such that the holes correspond to the respective counterbored holes 12a. The number of holes 11c is predetermined. In each hole 11c, a bundle member 21 is arranged. Each bundle member 21 serves as a heat-radiating member for radiating heat generated from the corresponding LED chip 6. In addition, a pair of holes 11d is formed in predetermined positions around the recess 11b such that the power cables 22a and 22b pass through the holes 11d, respectively.

Each bundle member 21 is formed in consideration of flexibility by making a plurality of wires 21a into a bundle. Each wire 21a is made of a metal having a high thermal conductivity, such as copper, aluminum, or silver. The diameter of each wire 21a is 0.1 mm or smaller. The number of wires 21a and the length of each wire 21a are properly set in consideration of heat capacity and workability depending on the type of endoscope.

In consideration of the workability, each end of each bundle member 21 is formed as a united portion 23 by, e.g., soldering or brazing, or using adhesive. According to the present embodiment, the number of united portions 23 arranged at the distal end of the endoscope 1 is eight. The surface at the distal end of each united portion 23 is flattened by polishing. On the other hand, the number of united portions 23 arranged adjacent to the proximal end of the endoscope 1 is four.

The recesses 11a and 11b are in communication with each other through a tapered hole 11e. The diameter of the tapered hole 11e adjacent to the distal end of the endoscope 1 is larger than that adjacent to the proximal end.

Figure 6:
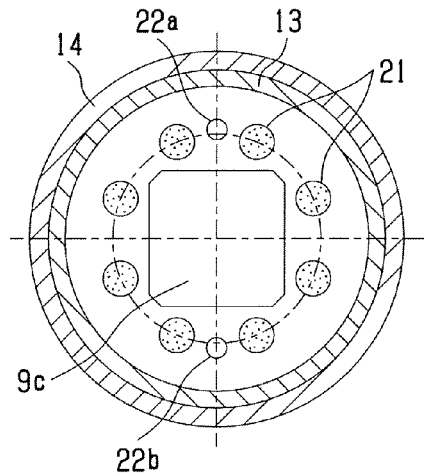
FIG. 6 is a sectional view at the line VI-VI of FIG. 2.

As shown in FIGS. 2 and 6, the lens frame holder 13 is substantially cylindrical. On the outer surface of the lens frame holder 13, an external thread segment 13a is formed in a predetermined position. The external thread segment 13a is screwed into an internal thread segment (17b in FIG. 2), which will be described below, formed in the connection fixing member 17. A through-hole 13b for the lens frame 9a, which constitutes the observation optical unit 10, is formed in the center of the lens frame holder 13 in the distal end portion thereof. In addition, heat-radiating member accommodation holes 13c are formed around the through-hole 13b such that the holes 13c correspond to the holes 11c, respectively. Each bundle member 21 is loosely fitted into the corresponding hole 13c.

The first connecting tube 14 includes a large-diameter portion 14a and a small-diameter portion 14b. The lens frame holder 13 is integrated with the second connecting tube 15. Specifically, the proximal end of the lens frame holder 13 is fitted into the distal inner surface of the large-diameter portion 14a of the first connecting tube 14. The outer surface of the small-diameter portion 14b is fitted into the distal inner surface of the second connecting tube 15.

The second connecting tube 15 is substantially tubular. The first connecting tube 14 and the bending portion 4 are integrally fitted into the second connecting tube 15. Specifically, the outer surface of the small-diameter portion 14b of the first connecting tube 14 is arranged on the distal inner surface of the second connecting tube 15. A distal-end bending piece 4a, a bending rubber 4b, and an external blade 4c constituting the bending portion 4 are arranged in predetermined positions in the proximal end portion of the second connecting tube 15. The bending rubber 4b and the external blade 4c are integrally fixed to the second connecting tube 15 by winding fixing members 31.

Figure 7:
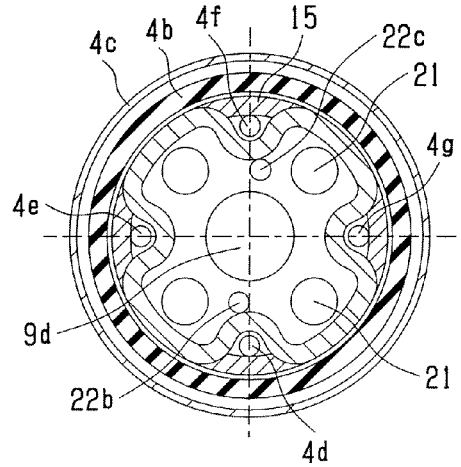
FIG. 7 is a sectional view at the line VII-VII of FIG. 2.

Referring to FIG. 7, a downward bending wire 4d, a leftward bending wire 4e, an upward bending wire 4f, and a rightward bending wire 4g are arranged in the bending portion 4.

Figure 1:
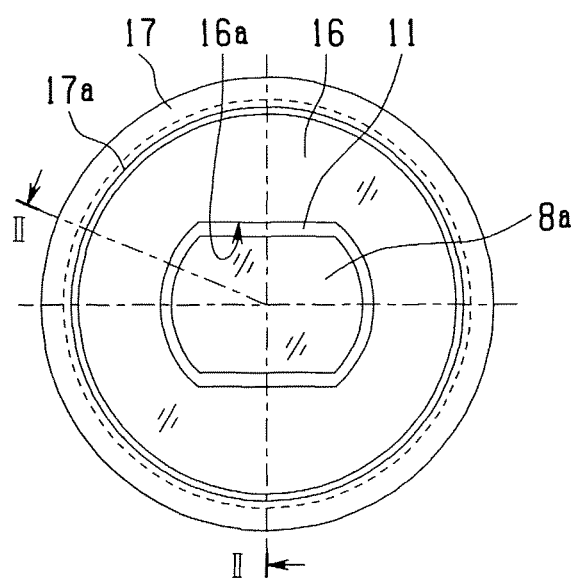
FIG. 1 is a front view of the distal end of an insertion unit according to a first embodiment of the present invention.

As shown in FIGS. 1 and 2, the cover glass 16 is made of, e.g., a substantially ring-shaped flat optical member. A through-hole 16a corresponding to the distal end of the objective holder 11 is formed in the center of the cover glass 16.

The connection fixing member 17 is substantially tubular. A fit portion 17a is formed on the inner circumference at the distal end of the connection fixing member 17. The fit portion 17a is in contact with the distal end of the cover glass 16. An internal thread segment 17b is formed in the proximal end portion of the connection fixing member 17 such that the external thread segment 13a formed in the lens frame holder 13 is screwed into the internal thread segment 17b.

Figure 8:
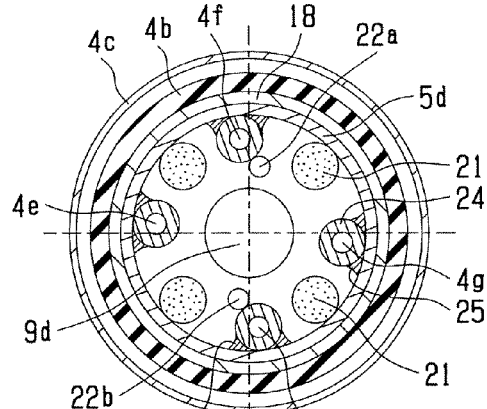
FIG. 8 is a sectional view at the line VIII-VIII of FIG. 2.

Referring to FIGS. 2, 7, and 8, the eight bundle members 21 respectively extend to the proximal end of the endoscope 1 through the holes 11c, the objective holder 11, the first connecting tube 14, and the second connecting tube 15. In order to be appropriate to the bending direction and a space in the pieces 4a, the eight bundle members 21 are combined into four bundle members 21 in the vicinity of the bending portion 4 such that two adjacent bundle members 21 are combined into one bundle. The four bundle members 21 extending through the bending portion 4 are arranged in the flexible tube 5. The four bundle members 21 in the flexible tube 5 have different lengths. Therefore, the respective united portions 23 of the four bundle members 21 are arranged in different positions in the flexible tube 5.

The flexible tube 5 includes a spiral tube 5a arranged on the inner surface of the tube 5, a mesh tube 5b covering the spiral tube 5a, and an external tube 5c covering the mesh tube 5b. The flexible tube 5 further includes a distal connector 5d at the distal end. The distal connector 5d is arranged on the inner surface of a third connecting tube 18 that constitutes the proximal part of the bending portion 4. Each of the bending wires 4d to 4g is extended through a coil component 24. The coil components 24 are integrally joined to predetermined portions on the inner surface of the distal connector 5d by brazing 25.

Figure 9:
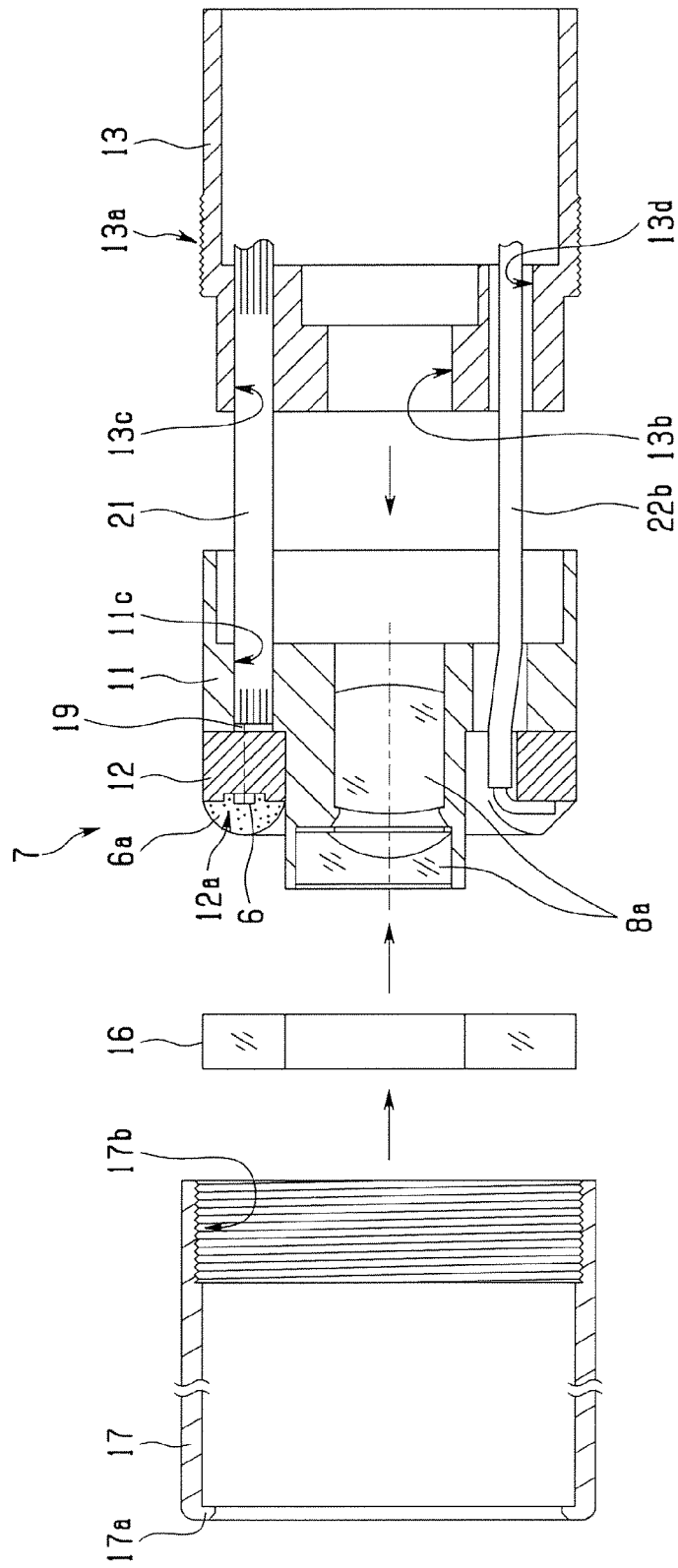
FIG. 9 is a diagram explaining a process of assembling a distal end portion.

A process of assembling the distal end portion 3 will now be described with reference to FIG. 9.

First, silicone grease 19 having a high thermal conductivity is applied to the inner surface of the LED substrate 12 constituting the LED illumination unit 7. In this state, the objective holder 11 in which the optical lenses 8a are disposed is come into contact with the inner surface of the LED substrate 12. After that, the united portions 23, serving as the distal ends of the bundle members 21 each including the predetermined number of wires 21a, are arranged in the holes 11c in the objective holder 11, respectively. In this instance, the distal end of each united portion 23 is closely attached to the proximal surface of the LED substrate 12, with the silicone grease 19 therebetween. The united portions 23 are fixed to the LED substrate 12 by soldering. The power cables 22a and 22b extending from the LED substrate 12 are arranged in the notches 12b, respectively.

Thus, the LED substrate 12 is in tight contact with the objective holder 1, with the silicone grease 19 therebetween. In addition, the bundle members 21 are arranged in tight contact with the objective holder 11 by soldering.

Instead of the silicone grease 19, a high-thermal-conductivity filler, a heat transfer sheet, or a heat transfer film may be used.

Subsequently, the cover glass 16 is attached to the distal-end surface of the LED substrate 12. The distal end of the lens frame holder 13 is inserted into a recess at the proximal end of the objective holder 11. In this instance, the bundle members 21 are inserted into the holes 13c, respectively.

Subsequently, the cover glass 16, the LED substrate 12, and the objective holder 11 are capped on their circumferences with the connection fixing member 17 in that order. Then, the distal end of the connection fixing member 17 reaches the vicinity of the external thread segment 13a formed at the lens frame holder 13. In this instance, the external thread segment 13a is screwed into the internal thread segment 17b formed at the connection fixing member 17. Thus, the connection fixing member 17 is fixed to the lens frame holder 13 in a predetermined screwed state.

Thus, the cover glass 16 is come into tight contact with the sealing compound 6a by a predetermined pressure and the LED substrate 12 is come into tight contact with the objective holder 11 by a predetermined pressure, so that they are assembled into one unit.

After that, the lens frame 9a including the CCD 9 is fixed to this unit and the unit is connected to the bending portion 4 through the first connecting tube 14 and the second connecting tube 15. In this manner, the endoscope 1 is formed.

The operation of the endoscope 1 with the above-described structure will now be explained.

First, the LED illumination unit 7 is supplied with power through the power cables 22a and 22b, so that the LED chips 6 arranged in the LED substrate 12 emit light. Thus, an observation area is illuminated by light. An optical image of the illuminated observation area is formed on the surface of the CCD 9 through the optical lenses 8a of the observation optical unit 10, thus obtaining an endoscopic image.

While endoscopic images are being observed, the insertion unit 2 of the endoscope 1 is moved to a target observation area. In this instance, the bending portion 4 is bent in a desired direction by appropriately manipulating bending-portion operating means (not shown). In the bending portion 4, the flexible bundle members 21 are extendedly arranged separately in consideration of the bending direction. Accordingly, the bending portion 4 is easily bendable.

The LED illumination unit 7 is continuously supplied with power, so that heat generated from the LED chips 6 is gradually transferred to the LED substrate 12. Thus, the temperature of the LED substrate 12 gradually increases. The heat transferred through the LED substrate 12 is further transferred to the bundle members 21 which are in tight contact with the rear of the LED substrate 12, with the silicone grease 19 therebetween. The heat is also transferred to the objective holder 11 arranged on the rear of the LED substrate 12.

The heat transmitted through the objective holder 11 is transferred to the sides of the bundle members 21, the sides being joined to the inner surfaces of the holes 11c formed at the objective holder 11 by soldering, respectively. Each bundle member 21 conducts the heat from the distal end thereof in the direction toward the proximal end.

As mentioned above, the heat generated by the LED chips is transmitted from the distal ends of the elongated bundle members in the direction toward the proximal ends through the LED substrate and the objective holder. Advantageously, the LED illumination unit can be prevented from being heated at a high temperature. In addition, the conduction of heat generated by the LED chips to the CCD can be prevented with reliability.

Consequently, an observation area is illuminated by the desired amount of light for a long time to obtain good endoscopic images without noises, so that endoscopic observation can be performed using the images.

Figure 10:
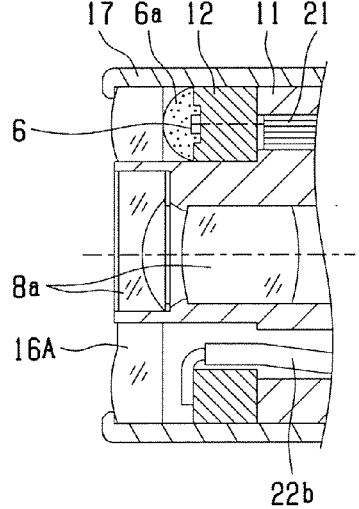
FIG. 10 is a diagram showing the distal end portion with a cover glass having a convex distal-end surface.
Figure 11:
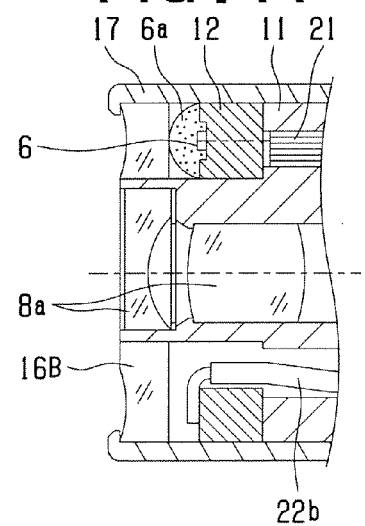
FIG. 11 is a diagram showing the distal end portion with a cover glass having a concave distal-end surface.

According to the present embodiment, the cover glass 16 is made of a flat optical member. The cover glass is not limited to that type. For example, a cover glass 16A having a convex distal-end surface as shown in FIG. 10 or a cover glass 16B having a concave distal-end surface as shown in FIG. 11 may be used.

In addition, the LED substrate 12 can be integrated with the objective holder 11.

Figure 12:
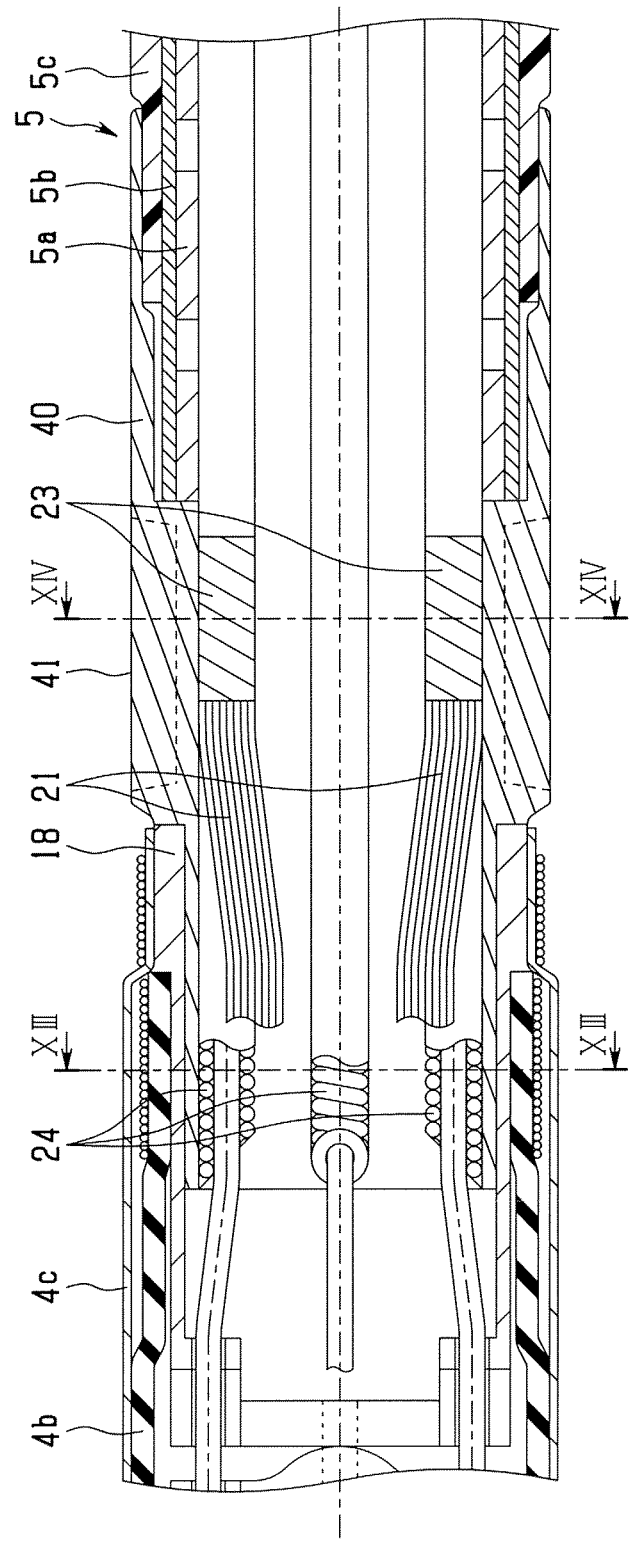
FIG. 12 is a sectional view explaining the structures of bundle members in the vicinity of a distal connector, the proximal end portion of each bundle member constituting a united portion joined to the distal connector.
Figure 13:
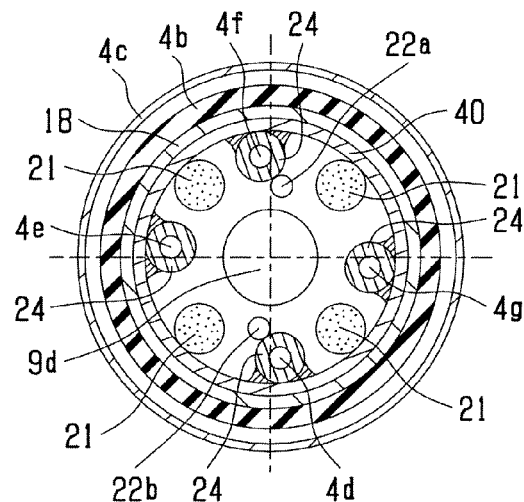
FIG. 13 is a sectional view at the line XIII-XIII of FIG. 12.
Figure 14:
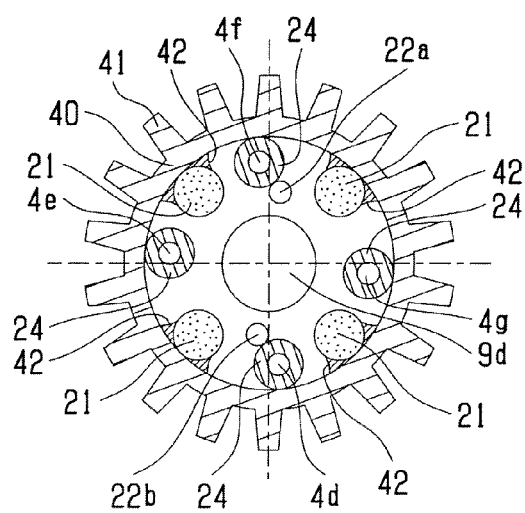
FIG. 14 is a sectional view at the line XIV-XIV of FIG. 12.
Figure 15:
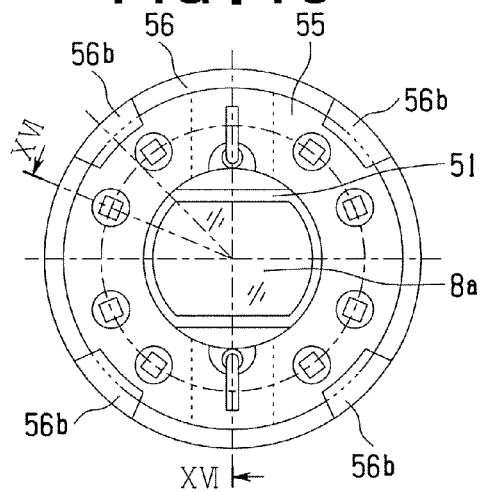
FIG. 15 is a front view of the distal end of an insertion unit according to a second embodiment of the present invention.
Figure 17:
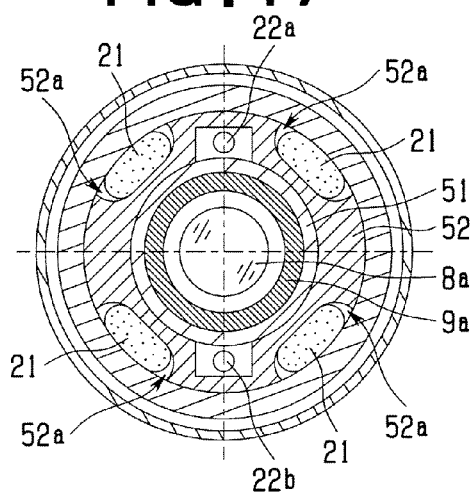
FIG. 17 is a sectional view at the line XVII-XVII of FIG. 16.
Figure 18:
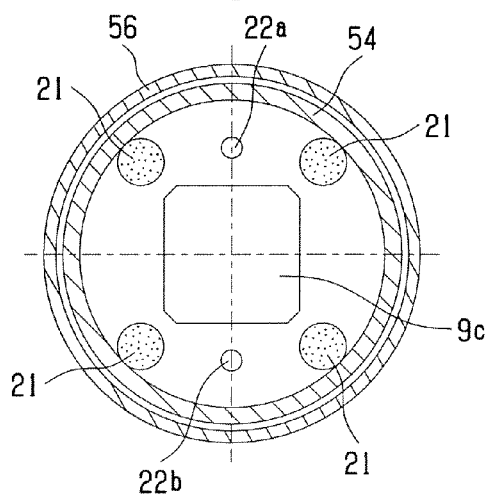
FIG. 18 is a sectional view at the line XVIII-XVIII of FIG. 16.
Figure 16:
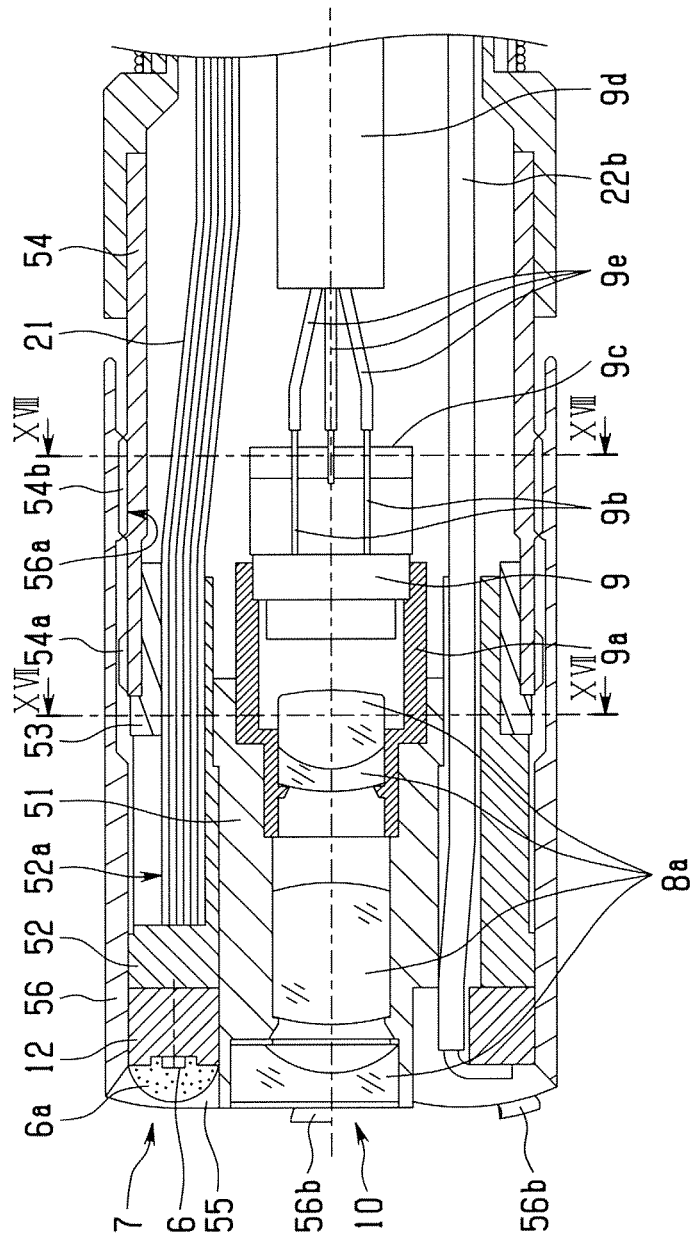
FIG. 16 is a sectional view at the line XVI-XVI of FIG. 15.
Figure 19:
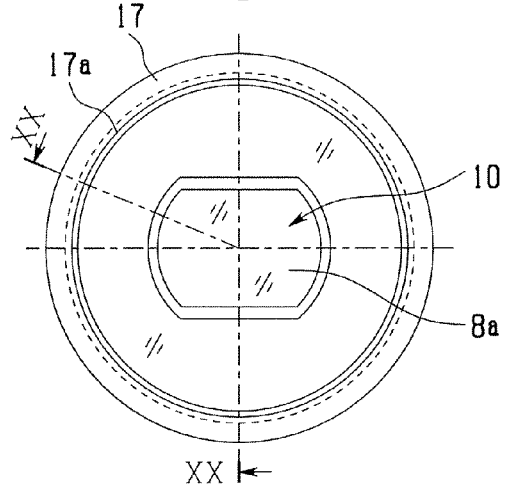
FIG. 19 is a front view of the distal end of an insertion unit of a rigid endoscope according to a third embodiment of the present invention.
Figure 21:
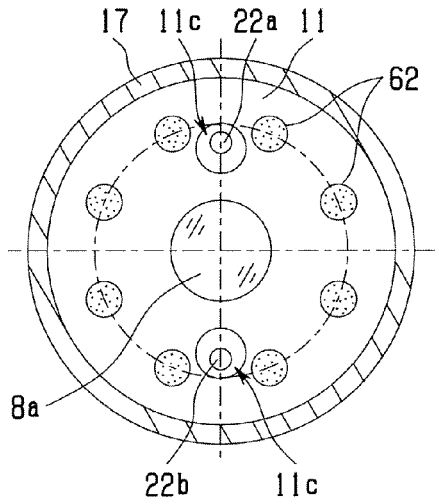
FIG. 21 is a sectional view at the line XXI-XXI of FIG. 20.
Figure 22:
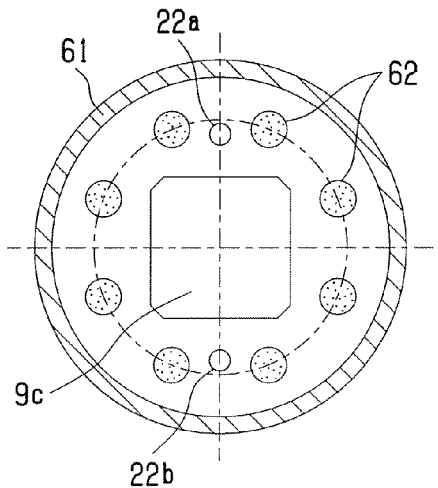
FIG. 22 is a sectional view at the line XXII-XXII of FIG. 20.

Instead of the arrangement of the proximal ends of the bundle members 21 in the flexible tube 5, as shown in FIGS. 12 to 14, the united portions 23 of the bundle members 21 may be joined to predetermined portions on the inner surface of a distal connector 40 using a joining material such as solder 42. The distal connector 40 has a cooling fin 41 on the outer surface.

Consequently, heat conducted through the bundle members 21 can be efficiently radiated from the distal connector 40, thus remarkably increasing the radiation effect of the bundle members 21.

In addition, each bundle member 21 may include a stranded wire or a wire mesh.

A second embodiment of the present invention will be described below with reference to FIGS. 15 to 18.

The objective holder 11 according to the first embodiment is made of a metal having a high thermal conductivity, such as copper or aluminum. According to the second embodiment, an objective holder dividingly includes an objective frame 51 made of a metal having a low thermal conductivity and an LED holder 52 made of a metal having a high thermal conductivity.

A ring member 53 is arranged at the proximal end of the LED holder 52. A tubular fixing member 54 is arranged on the outer surface of the ring member 53.

According to the second embodiment, a covering member 55 for further covering a sealing compound 6a overlaid on LED chips 6 is used instead of a cover glass.

Four notches 52a are formed in predetermined positions on the outer surface of the LED holder 52 to accommodate bundle members 21.

First and second external thread segments 54a and 54b, serving as a dual thread, are formed in predetermined positions on the outer surface of the tubular fixing member 54. The external thread segments 54a and 54b are screwed into an internal thread segment 56a formed in the proximal end portion of a connection fixing member 56 that is substantially tubular. Projections 56b are formed at the distal end of the connection fixing member 56 so that the projections 56b are come into contact with the covering member 55.

A process of assembling a distal end portion 3 will now be described.

First, silicone grease having a high thermal conductivity is applied to the proximal surface of an LED substrate 12 constituting an LED illumination unit 7. In this state, the objective frame 51 and the LED holder 52 in which optical lenses 8a are disposed are arranged in predetermined positions. After that, the four bundle members 21 are arranged in the notches 52a through-holes constituted of the LED holder 52 and the ring member 53. Solder or adhesive is supplied to openings of the notches 52a, thus fixing the bundle members 21 to the LED holder 52.

Thus, the LED substrate 12 is in tight contact with the objective frame 51, with the silicone grease therebetween. In addition, the bundle members 21 are arranged in tight contact with the LED holder 52, with, e.g., solder therebetween.

Subsequently, the tubular fixing member 54 is arranged on the outer surface of the ring member 53. The connection fixing member 56 caps the LED substrate 12, the LED holder 52, and the ring member 53 in that order. Then, the end of the connection fixing member 56 reaches the vicinity of the first external thread segment 54a formed at the tubular fixing member 54. In this instance, the first external thread segment 54a is screwed into the internal thread segment 56a formed at the connection fixing member 56.

After the internal thread segment 56a passes the first external thread segment 54a, the distal-end surface of the connection fixing member 56 reaches the vicinity of the second external thread segment 54b. Then, the second external thread segment 54b is screwed into the internal thread segment 56a. Thus, the connection fixing member 56 is fixed to the tubular fixing member 54.

Thus, the projections 56b of the connection fixing member 56 are come into contact with the covering member 55 by a predetermined pressure and the LED substrate 12, the LED holder 52, and the ring member 53 are come into contact with each other by a predetermined pressure, so that they are assembled into one unit.

After that, a lens frame 9a including a CCD 9 is joined to this unit and the unit is connected to a bending portion 4 through first and second connecting tubes 14 and 15. In this manner, an endoscope 1 according to the second embodiment is constructed.

Before the LED holder 52 is integrated with the objective frame 51, the lens frame 9a may be joined to the objective frame 51. The other structure and operation of the endoscope 1 according to the second embodiment are similar to those according to the first embodiment. The same components as those of the first embodiment are designated by the same reference numerals and a description thereof is omitted.

As mentioned above, the bundle members are arranged in the LED holder having the notches. In this state, the solder is supplied to the openings of the notches, thus joining integrally the bundle members to the LED holder. Accordingly, it is unnecessary to preliminarily process, e.g., flattening the distal-end surface of each bundle member. Advantageously, the workability can be improved.

In addition, the connection fixing member is fixed to the tubular fixing member by the double thread. Thus, the disconnection of the connection fixing member from the tubular fixing member can be prevented with higher reliability. Other advantages of the second embodiment are the same as those of the first embodiment.

The LED holder 52 may be integrated with the LED substrate 12.

A third embodiment of the present invention will now be described with reference to FIGS. 19 to 22.

The present embodiment relates to a rigid endoscope 60 including a rigid tube 61 instead of the foregoing bending portion 4. The rigid tube 61 has a predetermined length. The rigid endoscope 60 does not include the foregoing lens frame holder 13, first connecting tube 14, and second connecting tube 15. An external thread segment 61a formed in the distal end portion of the rigid tube 61 is screwed into an internal thread segment 17b of a connection fixing member 17, thus the rigid endoscope 60 being formed.

According to the third embodiment, instead of the bundle members 21, serving as heat-radiating members, rigid elongated rod members 62 having a high thermal conductivity, made of copper, aluminum, silver, or carbon graphite, are arranged in predetermined positions. Each rod member 62 has a predetermined cross section and further has a predetermined length. The other structure of the rigid endoscope 60 is substantially the same as that of the endoscope 1 according to the first embodiment.

The rigid tube 61 has holes 61b for the rod members and a through-hole 61c for a lens frame.

In the above-described rigid endoscope having a rigid insertion unit, rigid heat-radiating members are arranged instead of flexible heat-radiating members to conduct heat generated by LED chips from the distal ends of the respective rod members in the direction toward the proximal ends via an LED substrate and an objective holder, thus preventing an LED illumination unit from being heated at a high temperature. In addition, the heat generated from the LED chips can be prevented from being transferred to a CCD with reliability.

Figure 23:
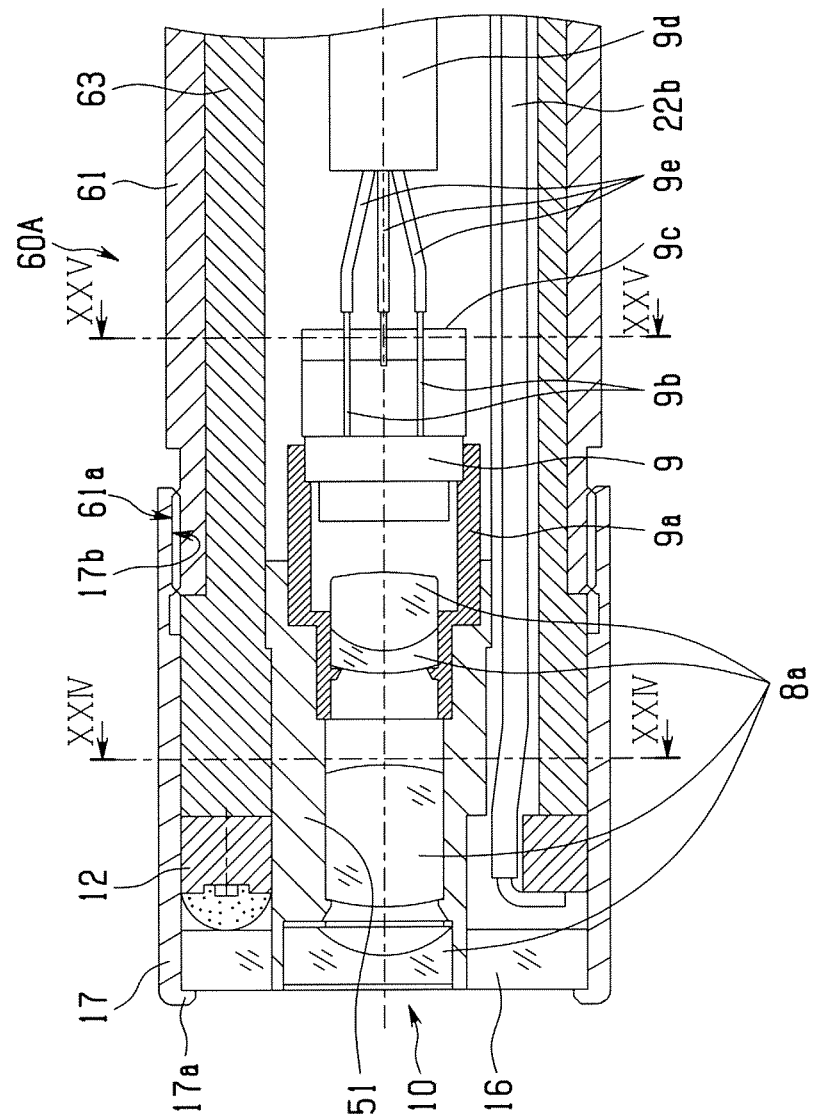
FIG. 23 is a longitudinal sectional view showing the structure of a rigid endoscope according to a modification of the third embodiment.
Figure 24:
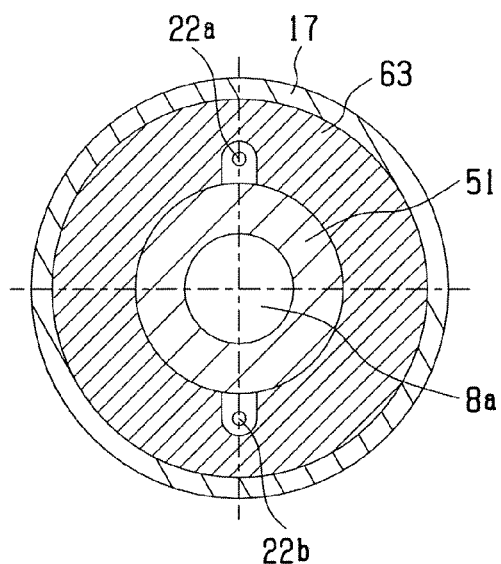
FIG. 24 is a sectional view at the line XXIV-XXIV of FIG. 23.
Figure 25:
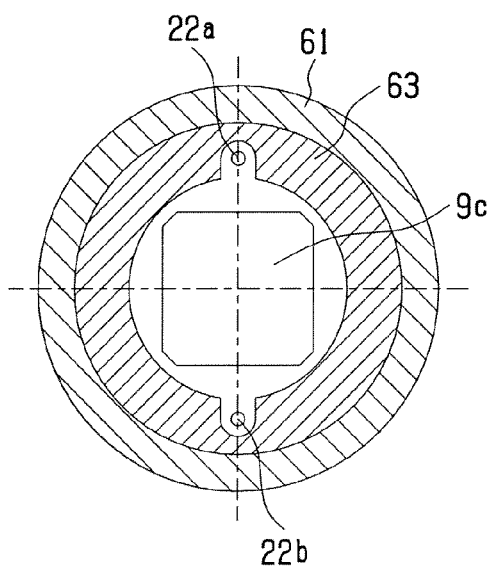
FIG. 25 is a sectional view at the line XXV-XXV of FIG. 23.

FIGS. 23 to 25 are diagrams explaining the structure of another rigid endoscope according to a modification of the second embodiment. As shown in the diagrams, a rigid endoscope 60A may include an objective frame 51 that is similar to that shown in FIGS. 15 to 17 and an elongated LED holder 63 that is substantially tubular and has a predetermined length.

Thus, the same operation and advantages as those of the second embodiment can be obtained.

A fourth embodiment of the present invention will now be described with reference to FIGS. 26 to 55.

Figure 26:
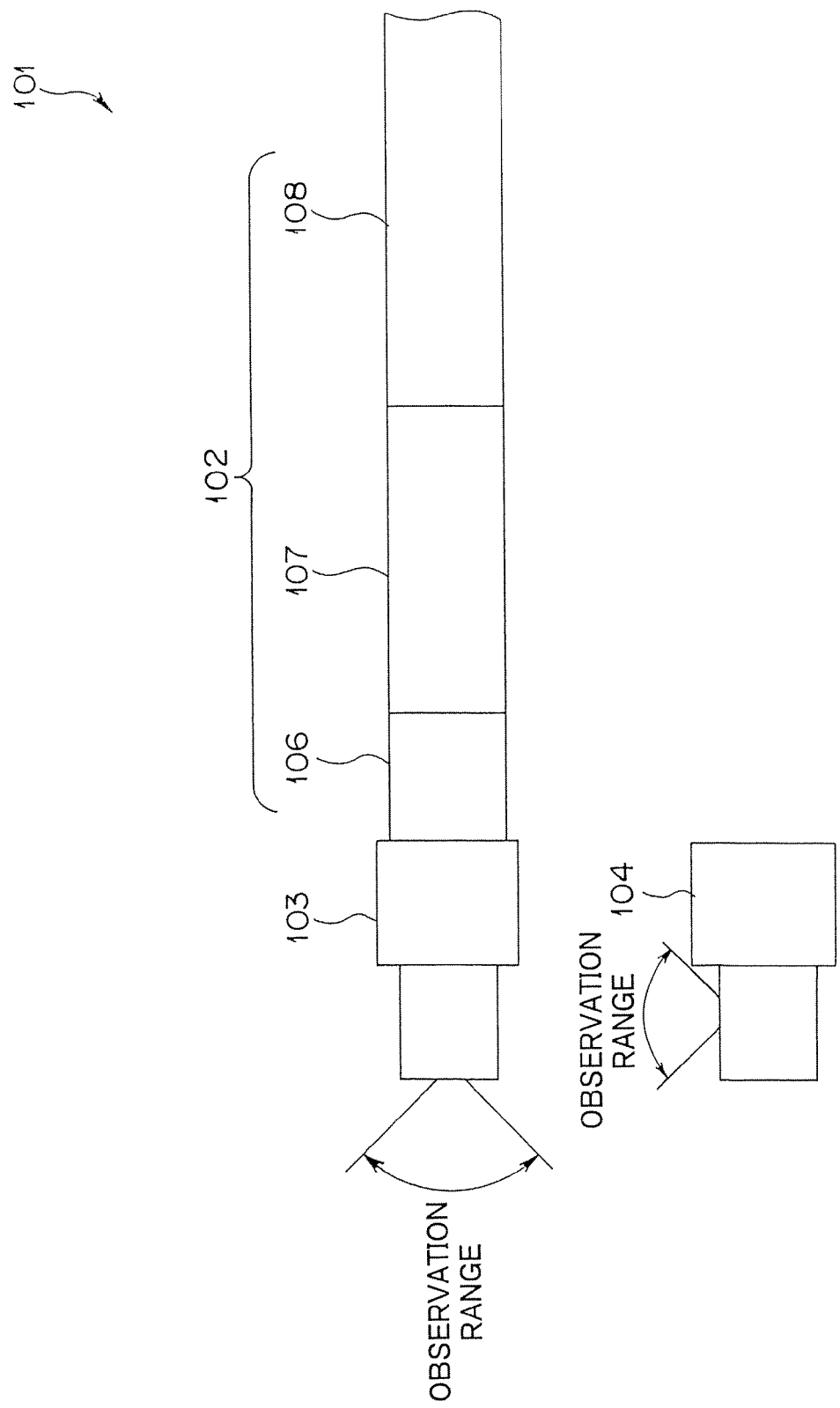
FIG. 26 is a diagram explaining the relationship between an insertion unit and a distal-end adapter according to a fourth embodiment of the present invention, two types of distal-end adapters being shown.
Figure 27:
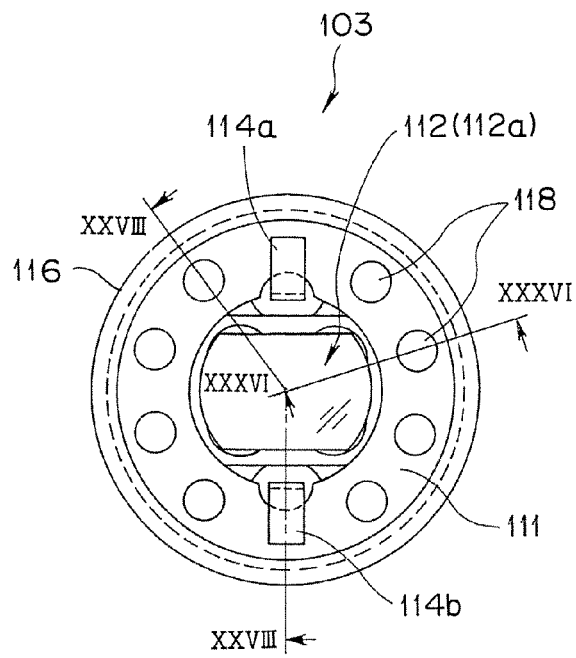
FIG. 27 is a front view of a direct-view type distal-end adapter.
Figure 28:
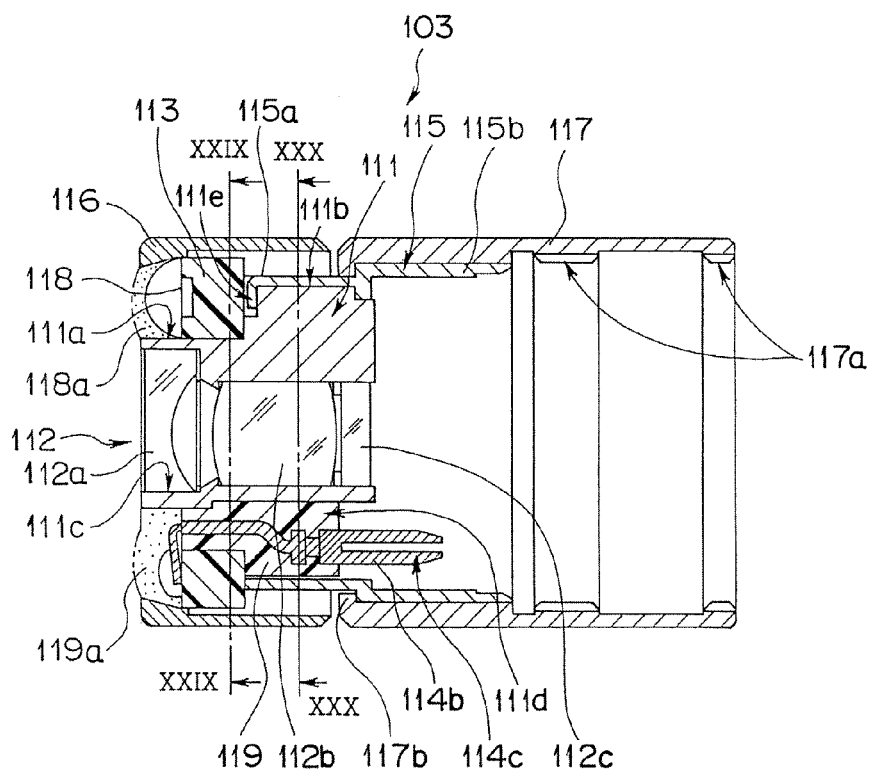
FIG. 28 is a sectional view at the line XXVIII-XXVIII of FIG. 27.
Figure 29:
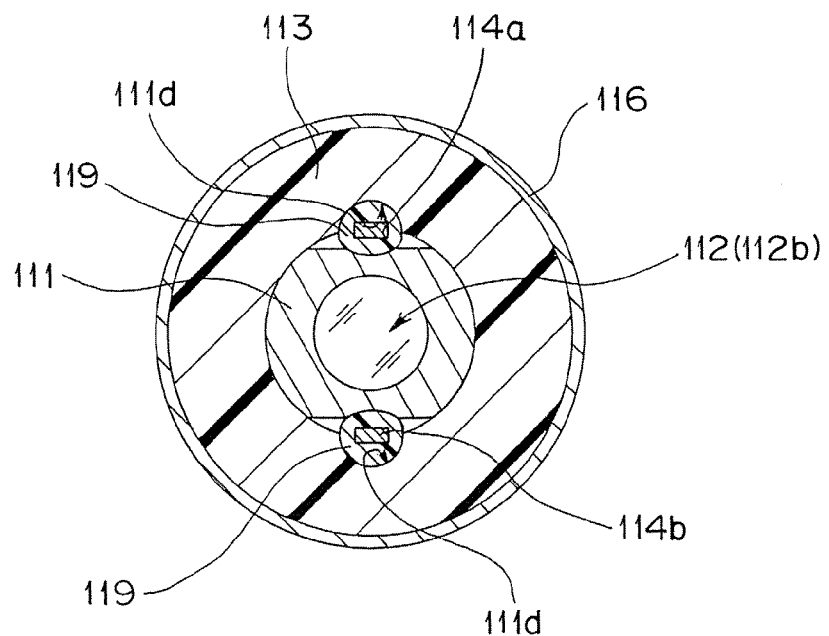
FIG. 29 is a sectional view at the line XXIX-XXIX of FIG. 28.
Figure 30:
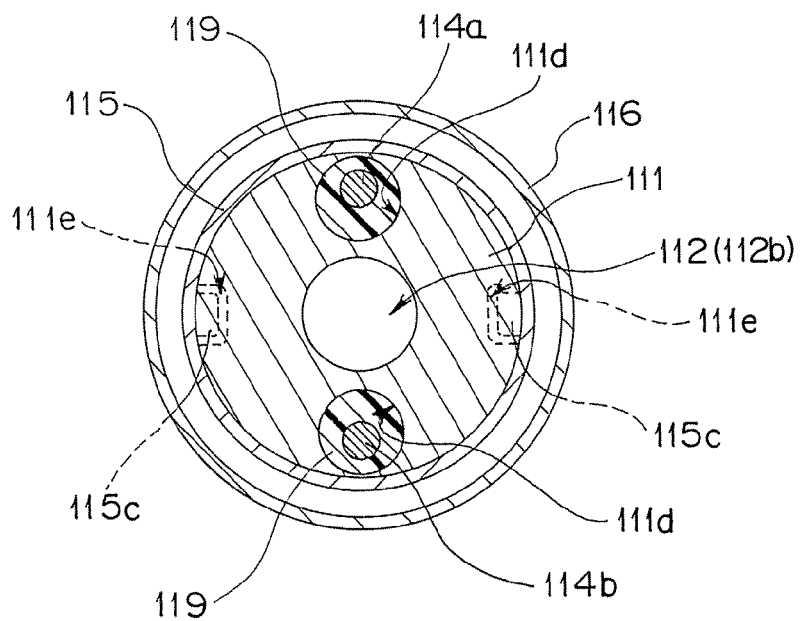
FIG. 30 is a sectional view at the line XXX-XXX of FIG. 28.
Figure 31:
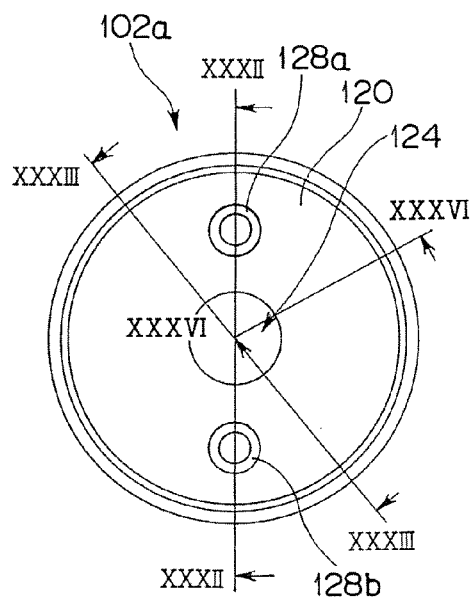
FIG. 31 is a front view of the insertion unit of the endoscope.
Figure 33:
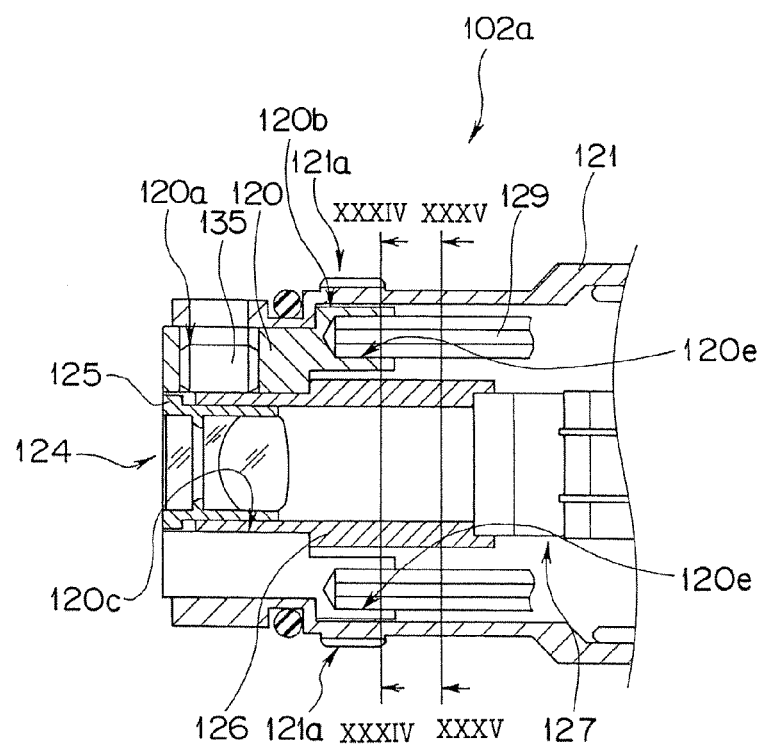
FIG. 33 is a sectional view at the line XXXIII-XXXIII of FIG. 31.
Figure 32:
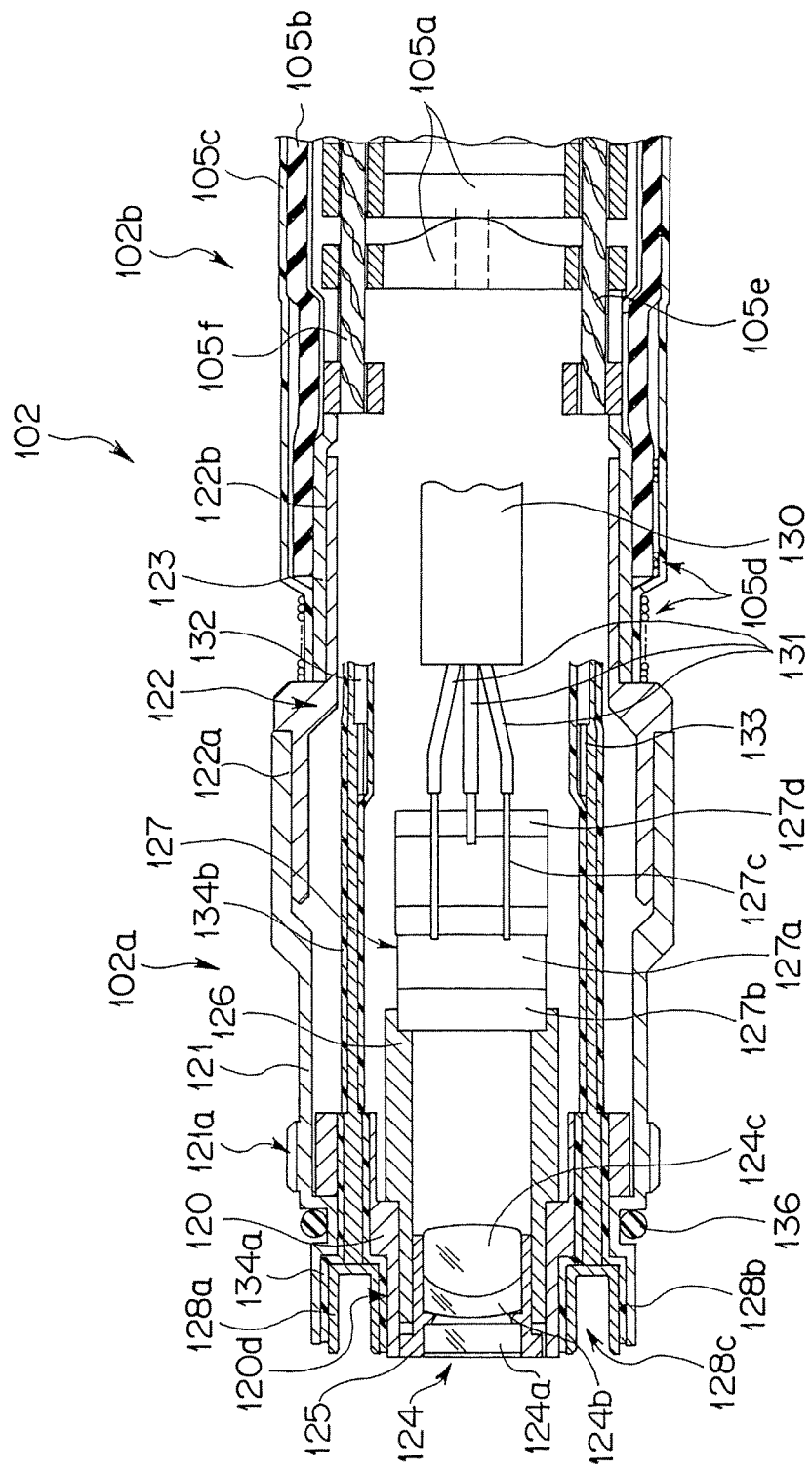
FIG. 32 is sectional view at the line XXXII-XXXII of FIG. 31.
Figure 34:
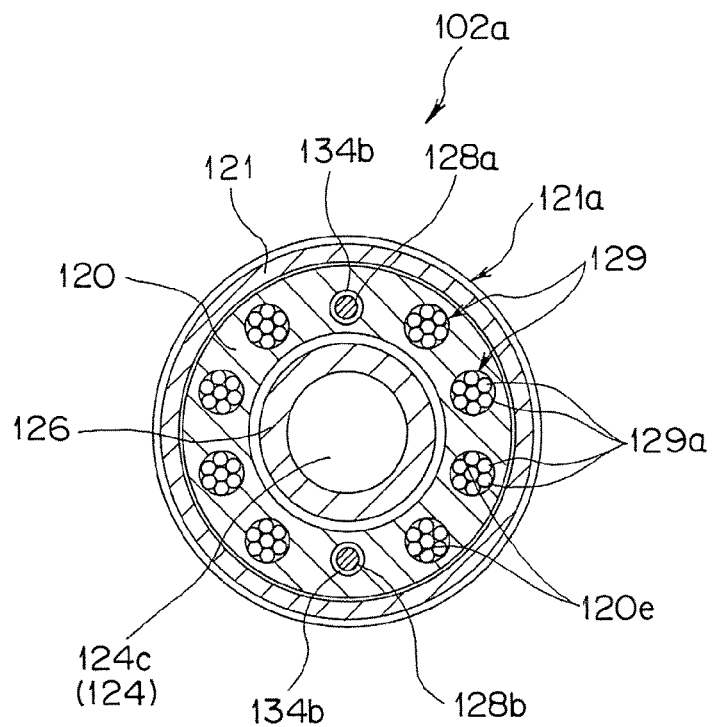
FIG. 34 is a sectional view at the line XXXIV-XXXIV of FIG. 33.
Figure 35:
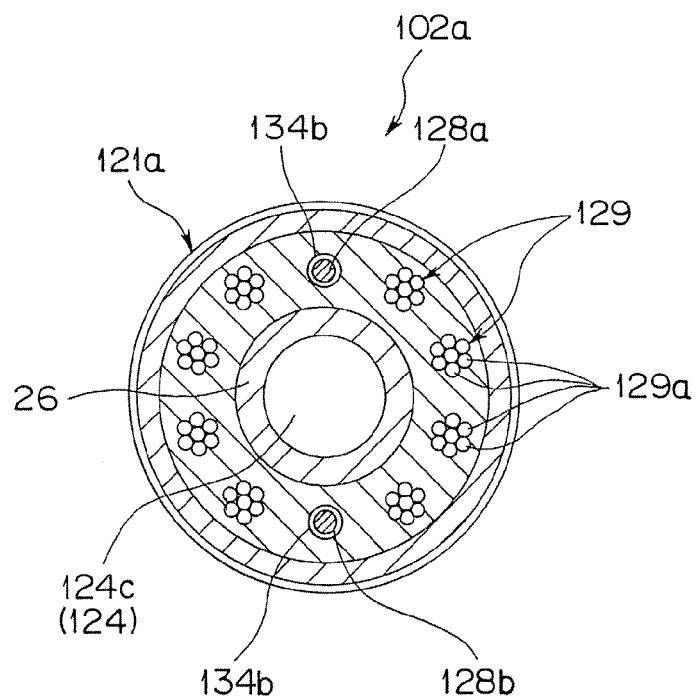
FIG. 35 is a sectional view at the line XXXV-XXXV of FIG. 33.

As shown in FIG. 26, an endoscope 101 according to the present embodiment has an elongated insertion unit 102. The insertion unit 102 includes a rigid distal end portion 106, a bending portion 107, and a flexible tube 108 connected in that order from the distal end. The bending portion 107 includes a plurality of bent pieces connected such that the bending portion 107 is bendable in the lateral and longitudinal directions. The flexible tube 108 is made of a flexible tubular member.

A direct-view type distal-end adapter 103, a side-view type distal-end adapter 104 or the like is selectively attachable to the distal end portion 106. The direct-view type distal-end adapter 103 includes a direct-view objective optical system, of which the range of observation is set in the longitudinal direction of the insertion unit. The side-view type distal-end adapter 104 includes a side-view objective optical system, of which the range of observation is set in the direction perpendicular to the longitudinal direction of the insertion unit.

The structure of the direct-view type distal-end adapter 103 will now be described with reference to FIGS. 27 to 30.

The direct-view type distal-end adapter 103 includes an adapter body 111, an objective optical unit 112, an LED substrate 113, adapter terminals 114, an adapter-body support member 115, a cover member 116, and an adapter release ring member (hereinafter, abbreviated to a ring member) 117.

The adapter body 111 is a first heat-radiating member made of a metal having a high thermal conductivity, such as copper or aluminum. The adapter body 111 is tubular and has a substantially convex cross section. In other words, the adapter body 111 includes a small-diameter portion 111a and a large-diameter portion 111b. In addition, a stepped central through-bore 111c is formed to substantially the center of the adapter body 111 in the longitudinal direction. A pair of holes 111d for accommodating the adapter terminals 114 is further formed in the adapter body 111.

The objective optical unit 112 includes optical lenses 112a to 112c arranged in the central through-bore 111c.

The LED substrate 113 is composed of, e.g., an aluminum circular plate having a central through-hole. A conductive pattern (not shown) is formed on one surface of the LED substrate 113. A plurality of LED illumination lights 118, serving as light emitting devices, and the one ends of the adapter terminals 114 are arranged in the conductive pattern. The LED substrate 113 is substantially in tight contact with the small-diameter portion 111a. The LED illumination lights 118, e.g., eight LED illumination lights 118 are arranged at regular intervals on a circumference at a predetermined distance from the center of the LED substrate 113. The LED illumination lights 118 in the radiation direction are covered with a translucent sealing compound 118a.

The adapter terminals 114 are one pair of metallic components constituting a first electric connecting unit. The one ends of the adapter terminals 114 are electrically connected to the conductive pattern. The other end of each adapter terminal 114 has a notch and functions as an elastic contact 114c. Each elastic contact 114c protrudes substantially perpendicularly with respect to the other surface of the LED substrate 113. One of the adapter terminals 114, i.e., an adapter terminal 114a serves as a power supply terminal. The other adapter terminal, i.e., an adapter terminal 114b serves as a ground terminal.

The adapter-body support member 115 is a stepped tubular member including a small-diameter portion 115a and a large-diameter portion 115b. The small-diameter portion 115a is arranged on the large-diameter portion 111b. The small-diameter portion 115a has embosses 115c at one end. The large-diameter portion 111b has recesses 111e corresponding to the embosses 115c. In other words, the embosses 115c are fitted into the recesses 111e, so that the adapter-body support member 115 is integrally attached to the adapter body 111.

The cover member 116 is a support member. Specifically, arranging the cover member 116 supports the LED substrate 113 on the adapter body 111.

The ring member 117 is freely rotatably arranged on the adapter-body support member 115. Internal thread segments 117a are formed on the inner surface of the ring member 117.

The ring member 117 has a bent portion 117b that is come into contact with a step formed between the small-diameter portion 115a and the large-diameter portion 115b of the adapter-body support member 115.

Insulating sealing resins 119 and 119a are used. The adapter holes 111d are filled with the sealing resin 119 such that the adapter terminals 114a and 114b are covered with the sealing resin 119. For this purpose, the adapter terminals 114 and the sealing resin 119 are integrally formed by, e.g., insert molding.

The structure of the distal end portion of the insertion unit will now be described with reference to FIGS. 31 to 35.

The distal end portion 106 includes an objective optical system holder (hereinafter, abbreviated to an objective holder) 120, a first connecting tube 121, a second connecting tube 122, a third connecting tube 123, an observation optical unit 124, a lens frame 125, a main frame 126, an image pickup device 127, insertion-unit terminals 128, and bundle members 129.

The objective holder 120 is a second heat-radiating member made of a metal having a high thermal conductivity, such as copper or aluminum. The objective holder 120 is tubular and has a substantially convex cross section. In other words, the objective holder 120 includes a small-diameter portion 120a and a large-diameter portion 120b. In addition, a central through-hole 120c is formed in substantially the center of the objective holder 120 in the axial direction. A pair of holes 120d for insertion-unit terminals 128a and 128b is further formed at the objective holder 120. The insertion-unit terminals 128a and 128b are electrically connected to the adapter terminals 114a and 114b, respectively.

Heat-radiating member accommodation holes 120e are formed at regular intervals on the proximal surface of the objective holder 120. The number of holes 120e is predetermined. In the holes 120e, the bundle members 129, serving as heat-radiating members for radiating heat conducted through the objective holder 120, are arranged. Each bundle member 129 is formed in consideration of flexibility by making a plurality of wires 129a, such as copper wires, aluminum wires, or silver wires, into a bundle. Each wire 129a has a high thermal conductivity and a diameter of 0.1 mm or smaller. The number of wires 129a and the length of each wire 129a are properly set in consideration of heat capacity and workability depending on the type of endoscope.

Both ends of each bundle member 129, i.e., the distal and proximal ends of wires 129a included in each member 129 are united in consideration of the workability by, e.g., soldering or brazing, or using adhesive. According to the fourth embodiment, eight united portions are arranged in the holes 120e, respectively.

Each of the first to third connecting tubes 121 to 123 is made of a highly corrosion resistant metal having a low thermal conductivity, such as stainless steel. An external thread segment 121a is formed on the outer surface of the first connecting tube 121, the external thread segment 121a being screwed into the internal thread segments 117a in the ring member 117.

The second connecting tube 122 is tubular and includes a large-diameter portion 122a and a small-diameter portion 122b on which the first and third connecting tubes 121 and 123 are integrally arranged. Specifically, the inner surface of the proximal end portion of the first connecting tube 121 is integrally fitted on the outer surface of the distal end portion of the large-diameter portion 122a of the second connecting tube 122. The inner surface of the distal end portion of the third connecting tube 123 is integrally fitted on the outer surface of the small-diameter portion 122b thereof.

The third connecting tube 123 is substantially tubular. The second connecting tube 122 and the bending portion 107 are integrally arranged on the third connecting tube 123. Specifically, the outer surface of the small-diameter portion 122b of the second connecting tube 122 is integrally fitted on the inner surface of the distal end portion of the third connecting tube 123. In predetermined positions in the proximal end portion of the third connecting tube 123, distal-end bending pieces 105a, a bending rubber 105b, and an external blade 105c which constitute the bending portion 107 are arranged. The bending rubber 105b and the external blade 105c are integrally fixed to the third connecting tube 123 by winding fixing members 105d. Downward and upward bending wires 105e and 105f are arranged in the bending portion 107.

The observation optical unit 124 includes, e.g., optical lenses 124a to 124c. The optical lenses 124a to 124c are fixed to the lens frame 125. A cover glass 127b constituting the image pickup device 127, which includes the lens frame 125 and a CCD 127a, is fixed to the main frame 126. Terminals 127c extending from the proximal end of the CCD 127a are electrically connected to signal lines 131 in predetermined positions, the signal lines 131 passing through a signal cable 130.

The main frame 126 is integrally fixed to the objective holder 120 by a fastening screw 135. Each of the lens frame 125 and the main frame 126 is made of a highly corrosion resistant metal having a low thermal conductivity, such as stainless steel.

The insertion-unit terminals 128a and 128b are metallic components constituting a second electric connecting unit. The insertion-unit terminals 128a and 128b have distal recesses 128c, serving as contacts to be come into electrical contact with the elastic contacts 114c of the adapter terminals 114a and 114b, respectively. The proximal ends of the insertion-unit terminals 128a and 128b are electrically connected to power supply cables 132 and 133 for supplying power to the LED illumination lights 118, respectively. Insulating members 134a and 134b are arranged on the outer circumferences of the insertion-unit terminals 128a and 128b, respectively.

The eight bundle members 129 extending toward the proximal end of the endoscope are combined in the vicinity of the bending portion 107 such that two adjacent bundle members 129 are combined into one bundle (not shown). The flexible tube 108 includes a spiral tube (not shown) arranged on the inner surface of the tube 108, a mesh tube (not shown) covering the spiral tube, and an external tube (not shown) covering the mesh tube. An O-ring 136 makes the connection between the direct-view type distal-end adapter 103 and the distal end portion 106 of the insertion unit 102 watertight.

Figure 37:
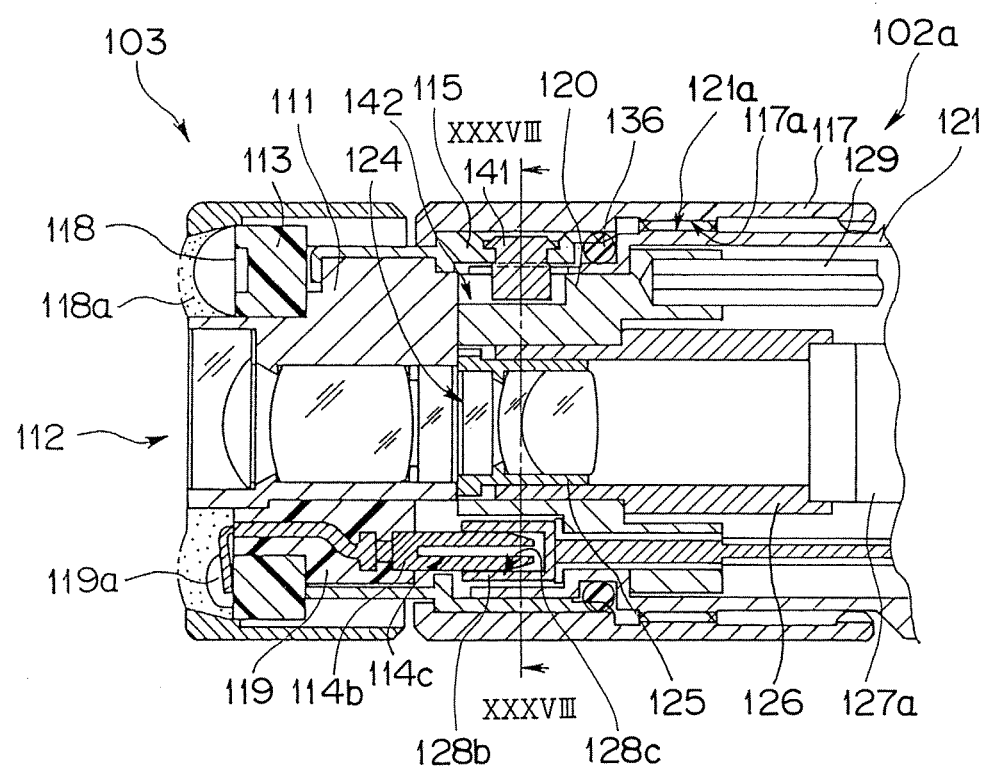
FIG. 37 is a diagram showing the direct-view type distal-end adapter attached to the distal end portion.
Figure 38:
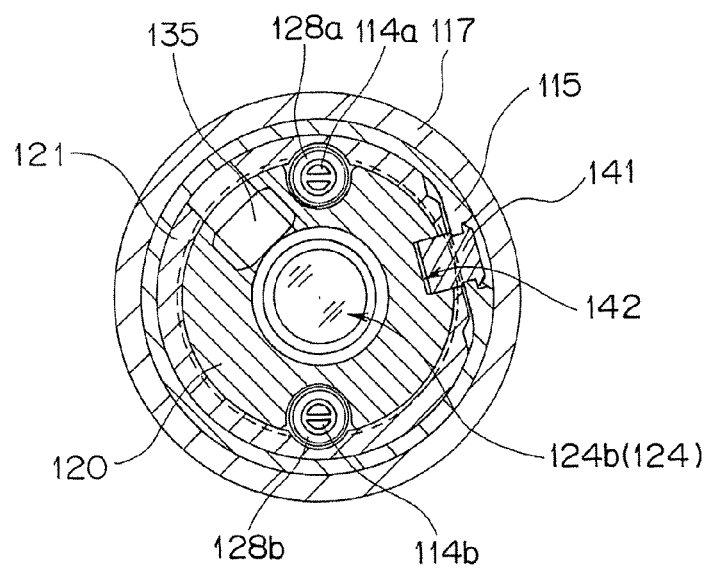
FIG. 38 is a sectional view at the line XXXVIII-XXXVIII of FIG. 37.

A process of connecting the direct-view type distal-end adapter 103 to the distal end portion 106 will now be described with reference to FIGS. 36 to 38.

Figure 36:
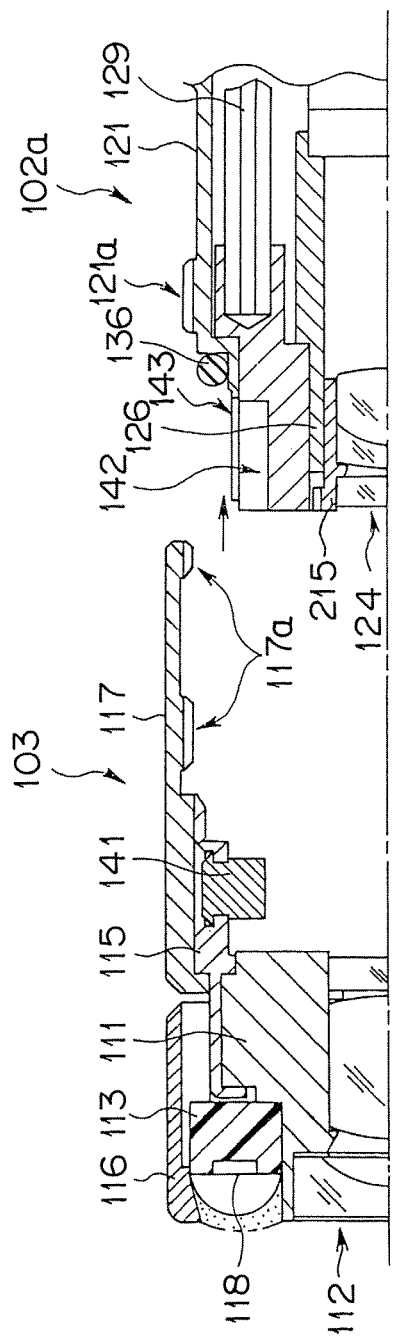
FIG. 36 is a diagram explaining the positional relationship between the direct-view type distal-end adapter shown in the sectional view at the line XXXVI-XXXVI of FIG. 27 and the distal end portion shown in the sectional view at the line XXXVI-XXXVI of FIG. 31.

Referring to FIG. 36, a positioning pin 141 is arranged in the adapter-body support member 115 constituting the direct-view type distal-end adapter 103. In addition, a positioning groove 142, which the positioning pin 141 is fitted into, is formed in the objective holder 120 constituting the distal end portion 106 of the insertion unit 102.

A notch 143 corresponding to the positioning groove 142 is formed in a predetermined position in the first connecting tube 121.

To attach the direct-view type distal-end adapter 103 to the distal end portion 106, the one internal thread segment 117a formed in the end portion of the ring member 117, constituting the direct-view type distal-end adapter 103, is made facing the external thread segment 121a formed at the first connecting tube 121, constituting the distal end portion 106. The external thread segment 121a is screwed into the internal thread segment 117a and, after that, the ring member 117 is rotated in a predetermined direction. Thus, the internal thread segment 117a crosses the external thread segment 121a, so that the direct-view type distal-end adapter 103 is loosely fitted to the distal end portion 106.

In this state, the positioning pin 141 on the direct-view type distal-end adapter 103 and the positioning groove 142 formed in the distal end portion 106 are made facing. Then, the positioning pin 141 is inserted into the positioning groove 142. In this state, the direct-view type distal-end adapter 103 is slid in the longitudinal direction.

Consequently, the elastic contacts 114c of the adapter terminals 114a and 114b are inserted into the distal recesses 128c of the insertion-unit terminals 128a and 128b, respectively. In this state, the direct-view type distal-end adapter 103 is further slid along the positioning groove 142 in the longitudinal direction. Thus, the elastic contacts 114c of the adapter terminals 114a and 114b are arranged deep in the distal recesses 128c in the distal end portions of the insertion-unit terminals 128a and 128b, so that the external thread segment 121a faces the internal thread segment 117a.

The ring member 117 is rotated in a predetermined direction. Thus, the external thread segment 121a is screwed into the other internal thread segment 117a, so that the direct-view type distal-end adapter 103 is moved in the longitudinal direction. Consequently, as shown in FIGS. 37 and 38, attaching of the direct-view type distal-end adapter 103 to the distal end portion 106 is complete.

In this instance, the elastic contacts 114c of the adapter terminals 114a and 114b are arranged in the distal recesses 128c of the insertion-unit terminals 128a and 128b, respectively, in a predetermined state. In addition, the objective optical unit 112 and the observation optical unit 124 are aligned such that the optical axis of the unit 112 substantially coincides with that of the unit 124. Further, the proximal surface of the adapter body 111 is in contact with the distal-end surface of the objective holder 120.

In this state, the LED illumination lights 118 are supplied with power through the power supply cables 132 and 133. The LED illumination lights 118 arranged in the LED substrate 113 are turned on, thus illuminating an observation area. Consequently, the optical image of the observation area illuminated by the illumination rays is formed on the surface of the CCD 127a through the optical lenses 112a to 112c of the objective optical unit 112 and those 124a to 124c of the observation optical unit 124, thus obtaining an endoscopic image.

The LED illumination lights 118 are continuously supplied with power, so that heat generated from the LED illumination lights 118 is gradually transferred to the LED substrate 113. Thus, the temperature of the LED illumination lights 118 gradually increases. The heat conducted through the LED substrate 113 is further transferred to the adapter body 111, the objective holder 120 in tight contact with the adapter body 111, and the bundle members 129 arranged on the proximal surface of the objective holder 120. The heat is transferred from the distal ends of the bundle members 129 in the direction toward the proximal ends and is then radiated.

As mentioned above, heat generated by the LED illumination lights in the direct-view type distal-end adapter is transmitted from the distal ends of the bundle members in the direction toward the proximal ends through the LED substrate, the adapter body, and the objective holder. Advantageously, the LED illumination lights can be prevented from being exposed to a high temperature.

Heat generated by the LED illumination lights is radiated. In addition, the lens frame and the image pickup frame (main frame) are made of a metal having a low thermal conductivity, such as stainless steel. Thus, the conduction of heat generated by the LED illumination lights to the CCD can be prevented with reliability.

Consequently, an observation area is illuminated by the desired amount of light for a long time using LED illumination lights to obtain good endoscopic images without noises, with which endoscopic observation can be performed.

According to the present embodiment, the direct-view type distal-end adapter has the positioning pin and the positioning groove is formed in the distal end portion of the insertion unit. Advantageously, the positional relationship between the direct-view type distal-end adapter and the distal end portion can be uniquely defined. Thus, the incorrect connection between the insertion-unit terminals and the adapter terminals can be surely prevented.

In addition, the position of the positioning pin is set such that the adapter terminals are electrically connected to the insertion-unit terminals by fitting the positioning pin into the positioning groove and then sliding the direct-view type distal-end adapter in the longitudinal direction. Advantageously, in attaching the direct-view type distal-end adapter to the distal end portion of the insertion unit, a trouble, e.g., the breakage of any adapter terminal or insertion-unit terminal can be reliably prevented.

According to the present embodiment, the electric connection between the adapter terminals 114 and the insertion-unit terminals 128 is achieved by inserting the elastic contacts 114c into the distal recesses 128c in the distal end portion 106 on condition that the direct-view type distal-end adapter 103 is attached to the distal end portion 106. The electric connection between the adapter terminals 114 and the insertion-unit terminals 128 is not limited to the insertion of the elastic contacts 114c into the distal recesses 128c. The following structures shown in FIGS. 39 to 43 may be used.

Figure 39:
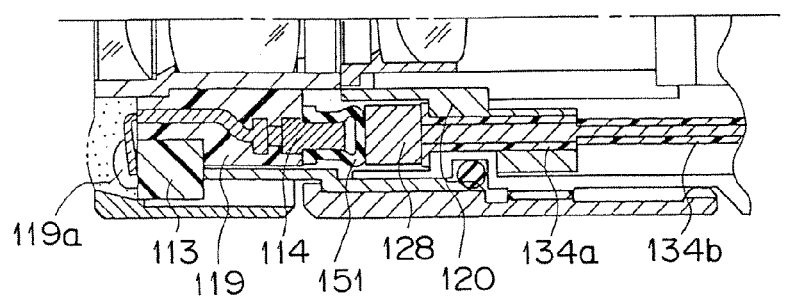
FIG. 39 is a diagram explaining the structure of another connection between each adapter terminal and the corresponding insertion-unit terminal.

In the structure of FIG. 39, an electric conductive rubber 151 is arranged at the proximal end of each adapter terminal 114. The electric conductive rubber 151 is come into tight contact with the flat surface of the corresponding insertion-unit terminal 128 to achieve the electric connection therebetween.

Figure 40:
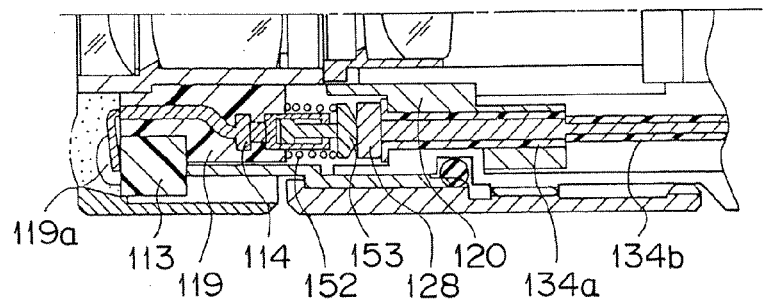
FIG. 40 is a diagram explaining the structure of another connection between each adapter terminal and the corresponding insertion-unit terminal.

In the structure of FIG. 40, a coil spring 152, functioning as biasing means, is arranged at the proximal end of each adapter terminal 114. A sliding terminal 153 having a convex surface is spring-biased to the flat surface of the corresponding insertion-unit terminal 128 by the coil spring 152, thus achieving the electric connection therebetween.

Figure 41:
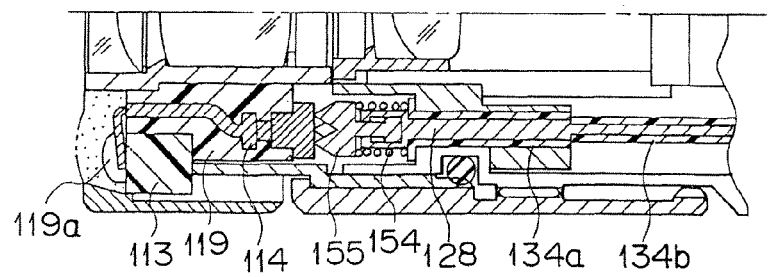
FIG. 41 is a diagram explaining the structure of another connection between each adapter terminal and the corresponding insertion-unit terminal.

In the structure of FIG. 41, a coil spring 154, functioning as biasing means, is arranged at the distal end of each insertion-unit terminal 128. A sliding terminal 155, of which end face has projections like contact pins, is spring-biased to the flat surface of the corresponding adapter terminal 114 by the coil spring 154, thus achieving the electric connection therebetween.

Figure 42:
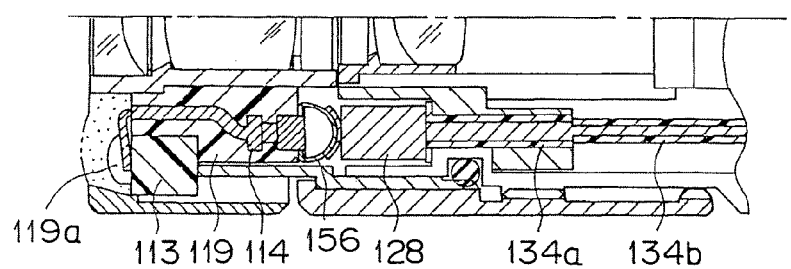
FIG. 42 is a diagram explaining the structure of another connection between each adapter terminal and the corresponding insertion-unit terminal.

In the structure of FIG. 42, a plate spring 156 having a semicircular cross section is arranged as an electrical contact having biasing means at the proximal end of each adapter terminal 114. The plate spring 156 is spring-biased to the flat surface of the corresponding insertion-unit terminal 128 to achieve the electric connection therebetween.

Figure 43:
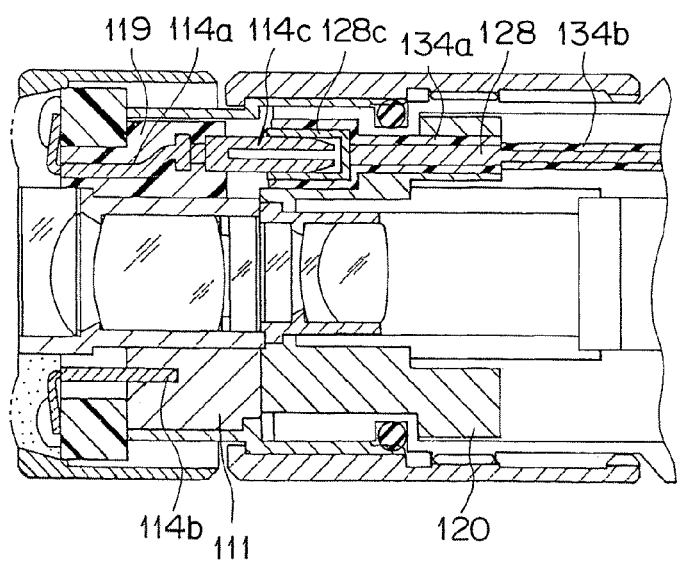
FIG. 43 is a diagram explaining the structure of another connection between each adapter terminal and the corresponding insertion-unit terminal.

In the structure of FIG. 43, the positive adapter terminal 114a is connected to the insertion-unit terminal 128 and the negative adapter terminal 114b is grounded to the adapter body 111, serving as a casing, thus achieving the electric connection between the adapter and the insertion unit.

Figure 44:
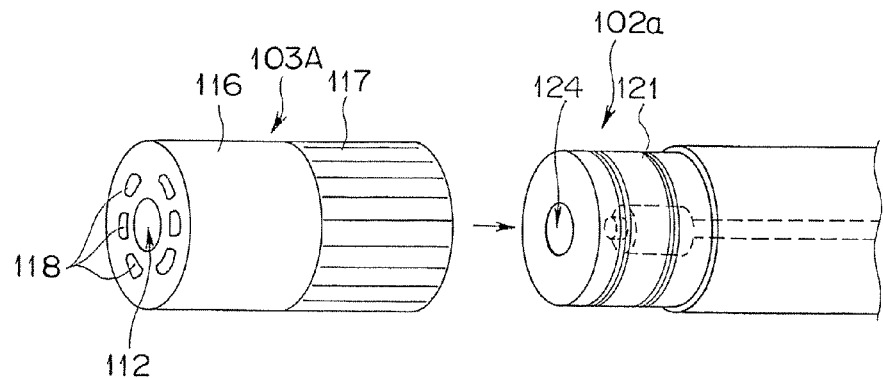
FIG. 44 is a diagram explaining an example of the arrangement of LED illumination lights in a direct-view type distal-end adapter.
Figure 45:
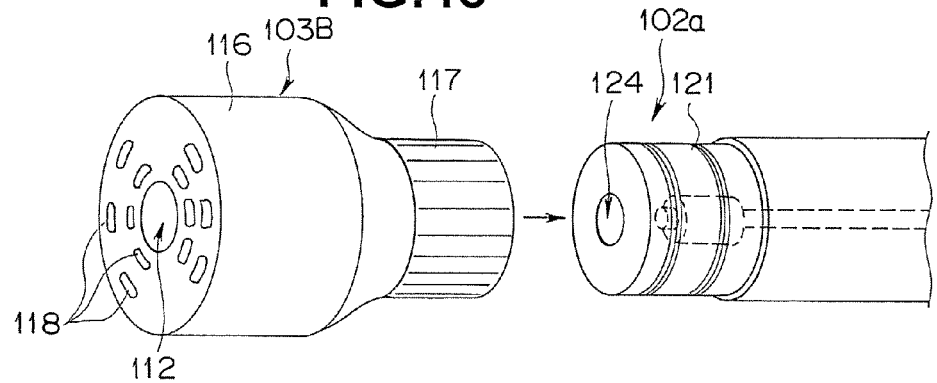
FIG. 45 is a diagram explaining an example of another arrangement of LED illumination lights in a direct-view type distal-end adapter.
Figure 46:
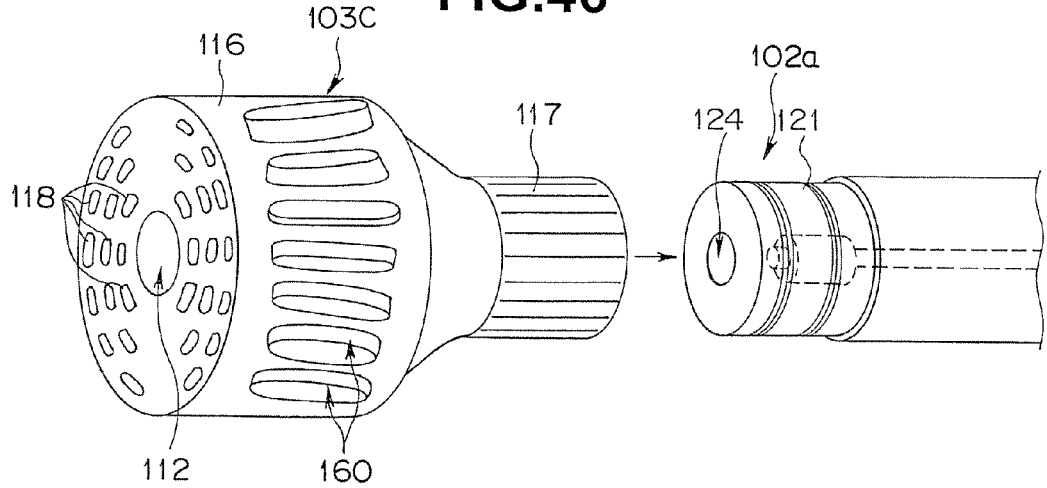
FIG. 46 is a diagram explaining an example of another arrangement of LED illumination lights in a direct-view type distal-end adapter.

According to the fourth embodiment, the eight LED illumination lights 118 are arranged at regular intervals on a circumference at a predetermined distance from the center of the distal-end surface of the direct-view type distal-end adapter 103. The arrangement of the LED illumination lights 118 is not limited to the above. However, as shown in FIGS. 44 to 46, various arrangement patterns are available. Referring to FIG. 44, a direct-view type distal-end adapter 103A has, e.g., six LED illumination lights 118 arranged at regular intervals on a circumference at a predetermined distance from the center of the end face of the adapter. Referring to FIG. 45, a direct-view type distal-end adapter 103B has LED illumination lights 118 arranged at regular intervals on two circumferences at predetermined distances from the center of the end face of the adapter. In each circle, six LED illumination lights 118 are arranged. Referring to FIG. 46, a direct-view type distal-end adapter 103C has LED illumination lights 118 arranged at regular intervals on three circumferences at predetermined distances from the center of the end face of the adapter. In the innermost circle, six LED illumination lights 118 are arranged. In the intermediate circle, ten LED illumination lights 118 are arranged. In the outermost circle, fourteen LED illumination lights 118 are arranged.

In the direct-view type distal-end adapter 103C of FIG. 46, a cooling fin 160 is arranged on the outer surface of the cover member 116 to dissipate heat generated by the LED illumination lights 118. Thus, the LED illumination lights 118 can be prevented from being exposed to a high temperature.

Figure 47:
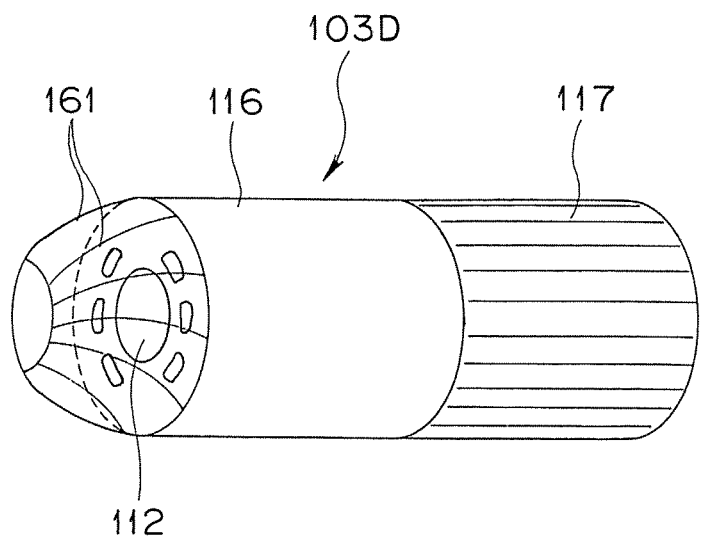
FIG. 47 is a diagram explaining a direct-view type distal-end adapter having a radial plate member in which a plurality of LED illumination lights are arranged.
Figure 48:
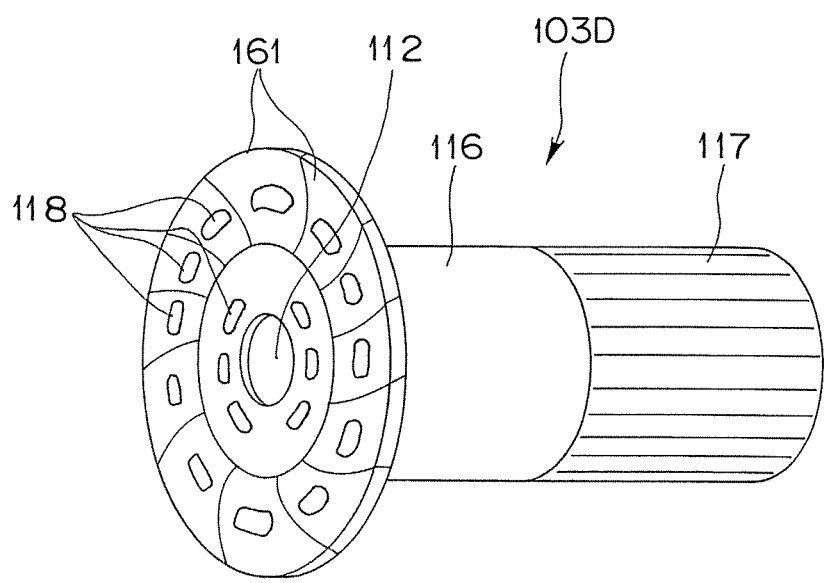
FIG. 48 is a diagram explaining the direct-view type distal-end adapter with the opened radial plate member having the LED illumination lights.
Figure 49:
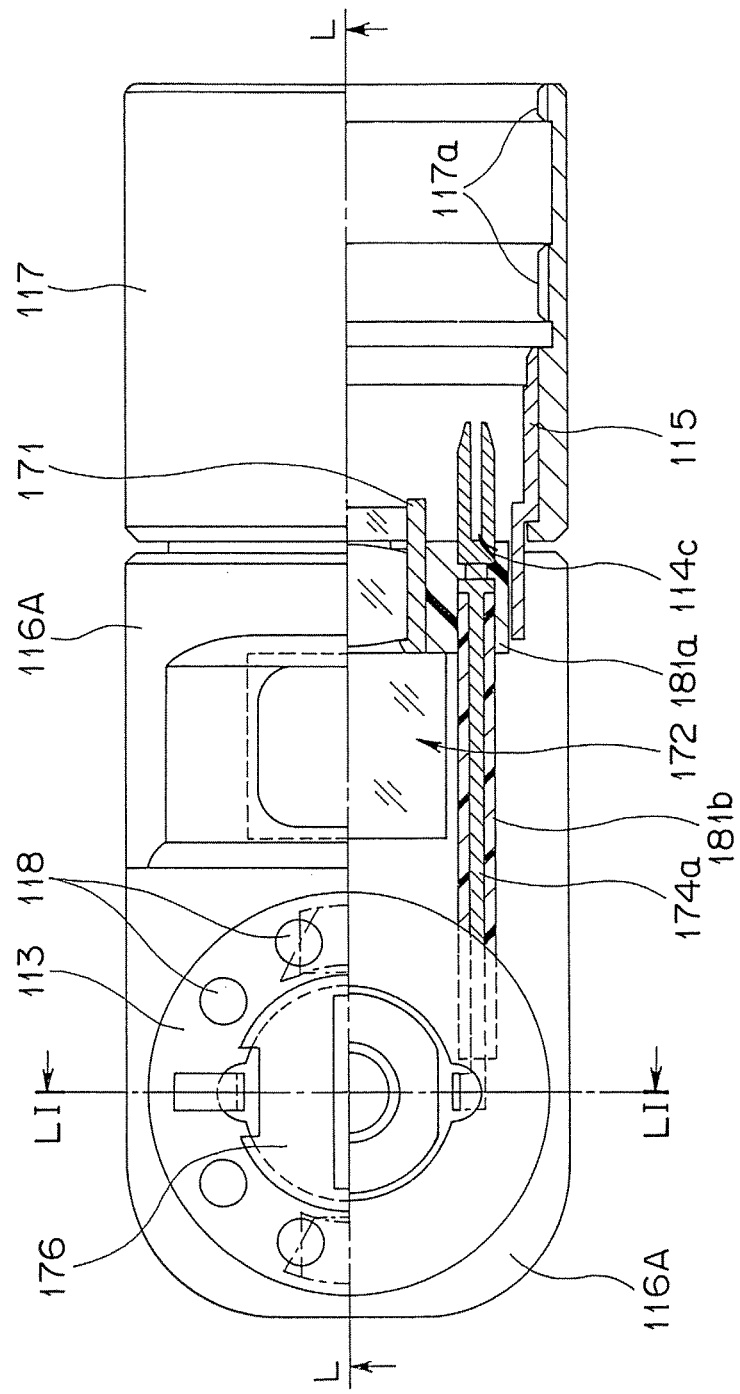
FIG. 49 is a diagram explaining a side-view type distal-end adapter.
Figure 50:
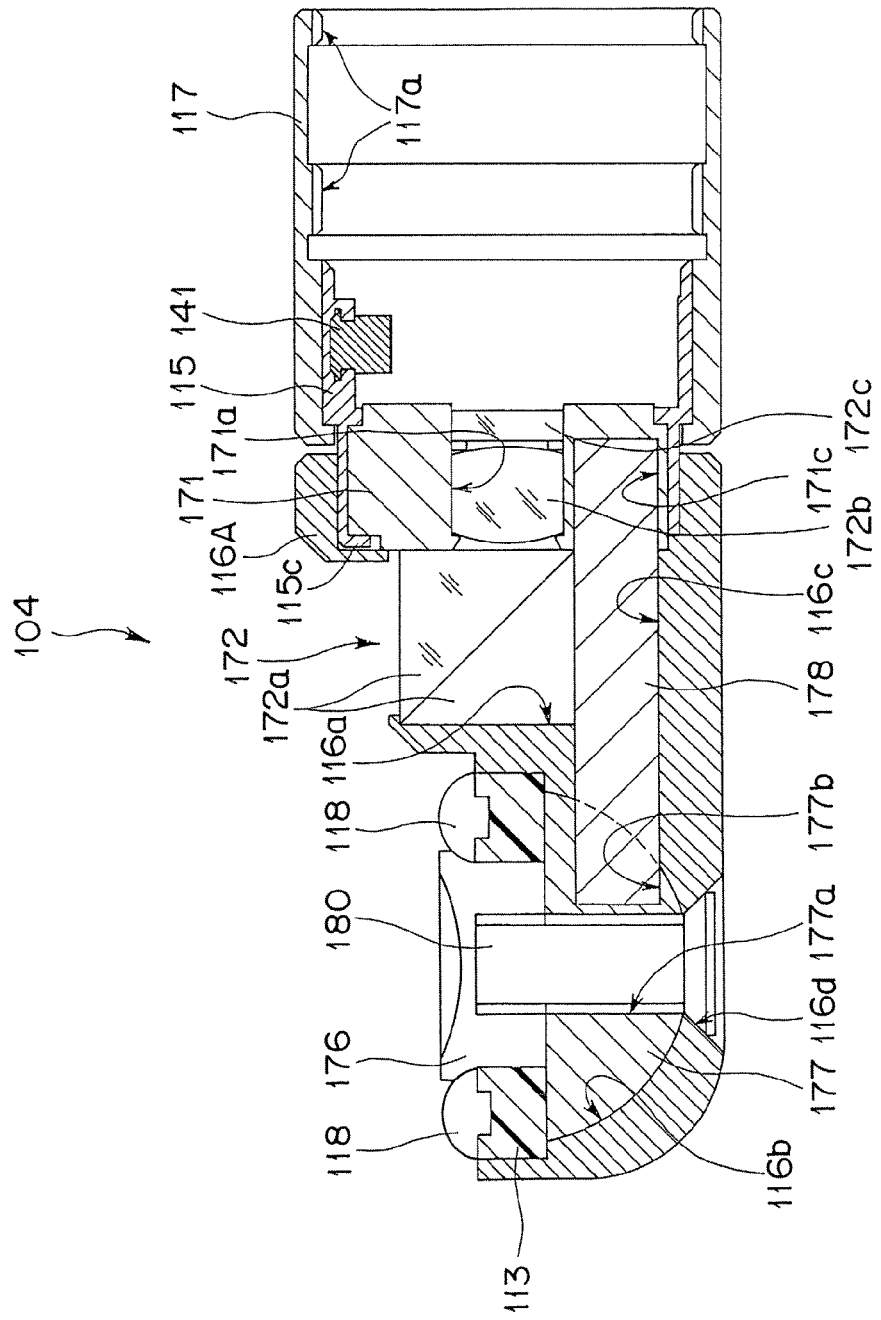
FIG. 50 is a sectional view at the line L-L of FIG. 49.
Figure 51:
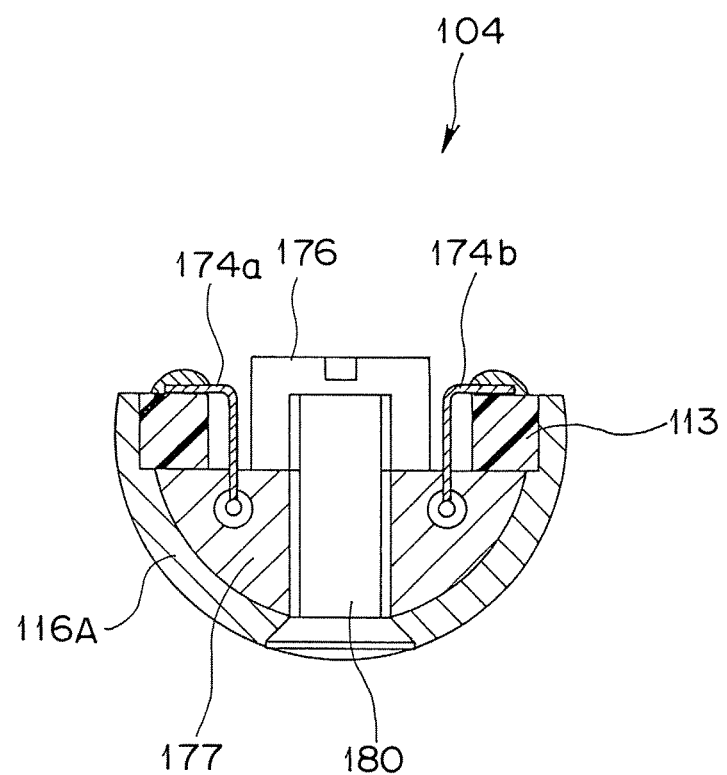
FIG. 51 is a sectional view at the line LI-LI of FIG. 49.

In addition, a radial plate member 161 having the LED illumination lights 118 on the inner surface may be arranged at the distal end of the cover member 116 as shown in FIG. 47. The radial plate member 161 is made of a shape memory alloy. The LED illumination lights 118 are supplied with power, so that the radial plate member 161 is deformed into a flaring shape, i.e., opened as shown in FIG. 48. Thus, the radial plate member 161 applies a large amount of illumination rays to an observation area.

The structure of the side-view type distal-end adapter 104 will now be described with reference to FIGS. 49 to 55.

The side-view type distal-end adapter 104 includes an adapter body 171, an objective optical unit 172, an LED substrate 113, a pair of adapter terminals 174a and 174b, an adapter-body support member 115, a cover member 116A, a retaining member 176, a ring member 117, a semispherical heat-conducting member 177, and a columnar heat-conducting member 178.

The adapter body 171 serves as a part of a first heat-conducting member and is made of a metal having a high thermal conductivity, such as copper or aluminum. The adapter body 171 is substantially tubular. In other words, a central through-hole 171a is formed in substantially the center of the adapter body 171. In addition, a pair of holes 171b for accommodating adapter terminals 174a and 174b and a hole 171c for accommodating the columnar heat-conducting member 178 are formed in the adapter body 171.

The objective optical unit 172 includes a mirror 172a that bends the optical axis at, e.g., a right angle and a plurality of optical lenses 172b and 172c, which are arranged in the central through-hole 171a.

The LED substrate 113 is, e.g., an aluminum circular plate having a central through-hole. The LED substrate 113 has a conductive pattern on one surface. In the conductive pattern, a plurality of LED illumination lights 118, serving as light emitting devices, and the one ends of the adapter terminals 174a and 174b are arranged. The LED substrate 113 is in tight contact with the flat surface of the semispherical heat-conducting member 177.

The adapter terminals 174a and 174b are a pair of metallic components constituting a first electric connecting unit. The other end of each of the adapter terminals 174a and 174b includes an elastic contact 114c having a notch.

The cover member 116A functions as a support made of a metal having a low thermal conductivity. The cover member 116A includes a recess 116a, a spherical recess 116b, and a hole 116c. In the recess 116a, the mirror 172a is arranged. In the spherical recess 116b, the semispherical heat-conducting member 177 is arranged. In the hole 116c, the columnar heat-conducting member 178 is arranged. In addition, the cover member 116A includes a countersink 116d which communicates with the spherical recess 116b.

Specifically, the retaining member 176 is fixed to the cover member 116A by a screw 180 passing through a through-hole 177a in the semispherical heat-conducting member 177 arranged in the spherical recess 116b, so that the semispherical heat-conducting member 177, the LED substrate 113, and the retaining member 176 are fixed to the cover member 116A.

The semispherical heat-conducting member 177 serves as a part of the first heat-conducting member and is made of a metal having a high thermal conductivity, such as copper or aluminum. The semispherical heat-conducting member 177 has the through-hole 177a, to which the screw 180 is inserted.

The columnar heat-conducting member 178 constitutes a part of the first heat-conducting member. The columnar heat-conducting member 178 is a rectangular or cylindrical column made of a metal having a high thermal conductivity, such as copper or aluminum. The columnar heat-conducting member 178 is arranged in the hole 116c of the cover member 116A.

The semispherical heat-conducting member 177 has a hole 177b which the end of the columnar heat-conducting member 178 is fitted into.

The other structure is the same as that of the direct-view type distal-end adapter 103. The same components as those of the adapter 103 are designated by the same reference numerals and a description thereof is omitted.

The side-view type distal-end adapter is constructed as mentioned above. When the external thread segment formed in the distal end portion of the first connecting tube is screwed into an internal thread segment formed on the ring member of the side-view type distal-end adapter, the adapter can be attached to the distal end portion of the endoscope. In this instance, the elastic contacts of the adapter terminals are fitted into the recesses of the insertion-unit terminals arranged in the distal end portion in a predetermined state.

Heat generated by the LED illumination lights is actively transferred to the LED substrate, the semispherical heat-conducting member, the columnar heat-conducting member, and the adapter body. After that, the heat is further transferred to the objective holder 120 and the bundle members 129 arranged in the distal end portion, so that the heat is radiated.

Consequently, the side-view type distal-end adapter 104 or the direct-view type distal-end adapter 103 can be selectively attached to the distal end portion 106.

When the side-view type distal-end adapter 104 is attached to the distal end portion 106, the optical characteristics of the endoscope with the side-view type distal-end adapter 104 are different from those of the endoscope with the direct-view type distal-end adapter 103 under observation. However, the same operation and advantages as those of the endoscope with the direct-view type distal-end adapter 103 can be obtained.

Figure 52:
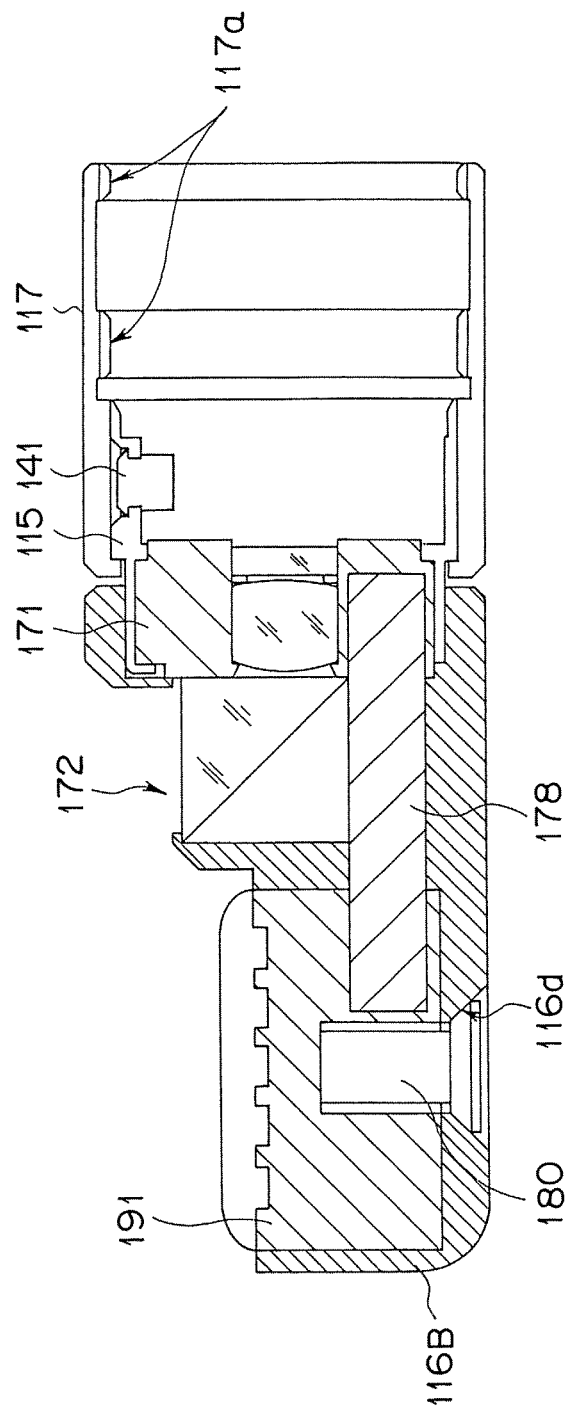
FIG. 52 is a longitudinal sectional view of another side-view type distal-end adapter.
Figure 53:
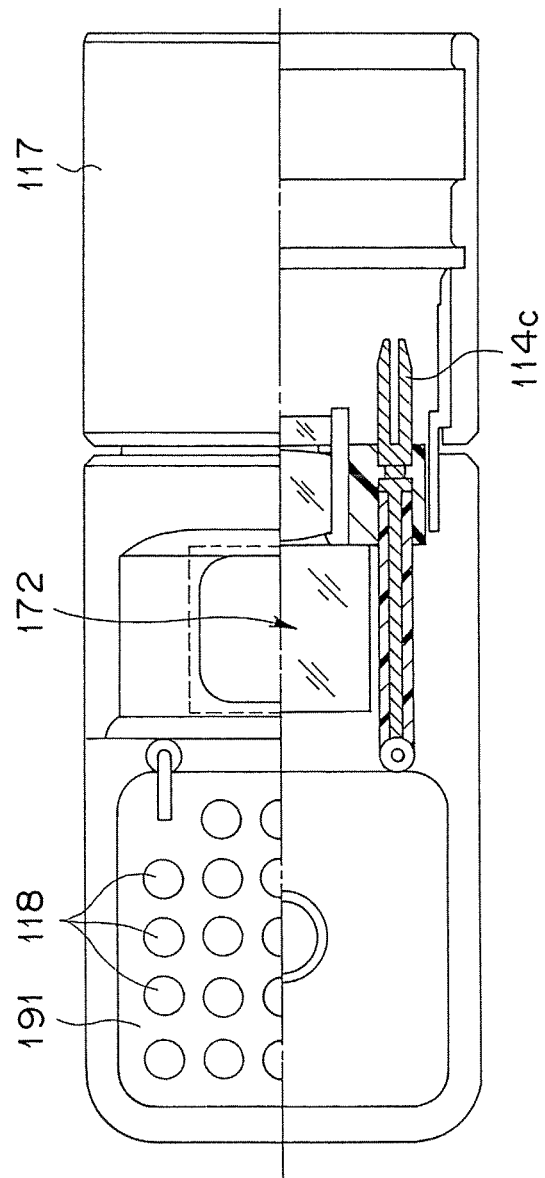
FIG. 53 is a front view of the side-view type distal-end adapter of FIG. 52.

As shown in FIGS. 52 and 53, an LED substrate 191 may be directly arranged in a cover member 116B so that heat generated by the LED illumination lights 118 is transferred through the LED substrate 191, the columnar heat-conducting member 178, and the adapter body 171 to the objective holder 120 and the bundle members 129 arranged in the distal end portion 106 to radiate the heat. In this case, the LED substrate 191 is rectangular and the LED illumination lights 118 are arranged in a matrix on one surface of the LED substrate 191. Thus, the same heat radiation effect as that in the foregoing structure can be obtained. In addition, the number of components can be reduced and the amount of illumination rays can be increased.

Figure 54:
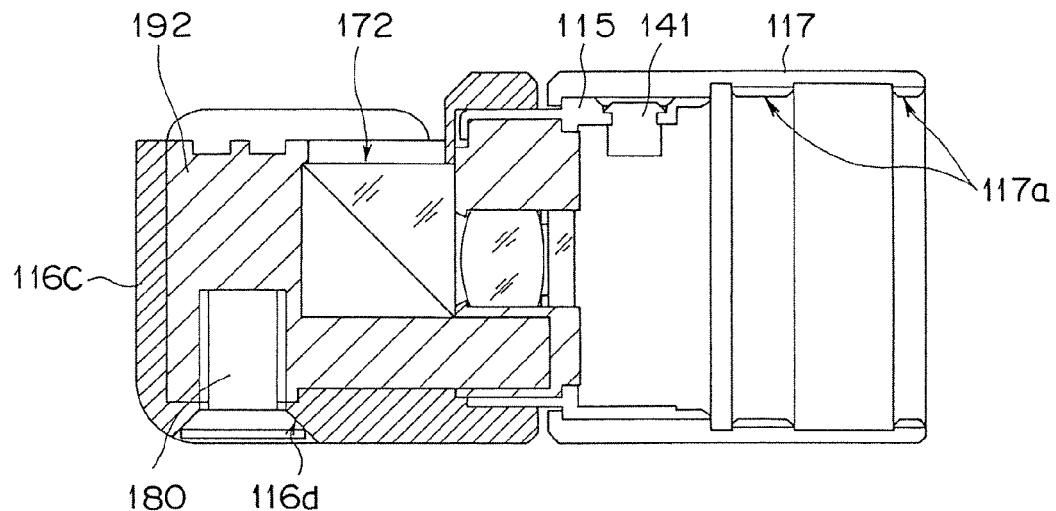
FIG. 54 is a longitudinal sectional view of another side-view type distal-end adapter.
Figure 55:
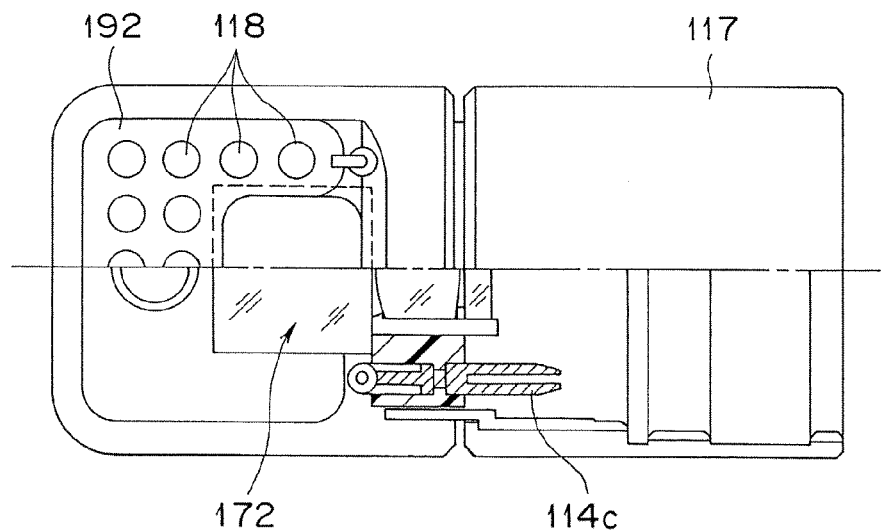
FIG. 55 is a front view of the side-view type distal-end adapter of FIG. 54.

As shown in FIGS. 54 and 55, an LED substrate 192 can be directly arranged in a cover member 116C. The LED substrate 192 may have a space in which the mirror 172a is arranged and the LED illumination lights 118 may be arranged in the vicinity of the mirror 172a. Thus, the same heat radiation effect as those of the foregoing structures can be obtained. In addition, the number of components can be reduced and the length of the side-view type distal-end adapter can be reduced.

According to the present embodiment, the direct-view type and side-view type distal-end adapters have been described. The distal-end adapter is not limited to the above types. A distal-end adapter of which field of view is set in another direction, e.g., an oblique forward view distal-end adapter may be used.

In the above-described embodiments, LEDs are used as light emitting devices. A light emitting device is not limited to an LED. A laser diode may be used.

Figure 56:
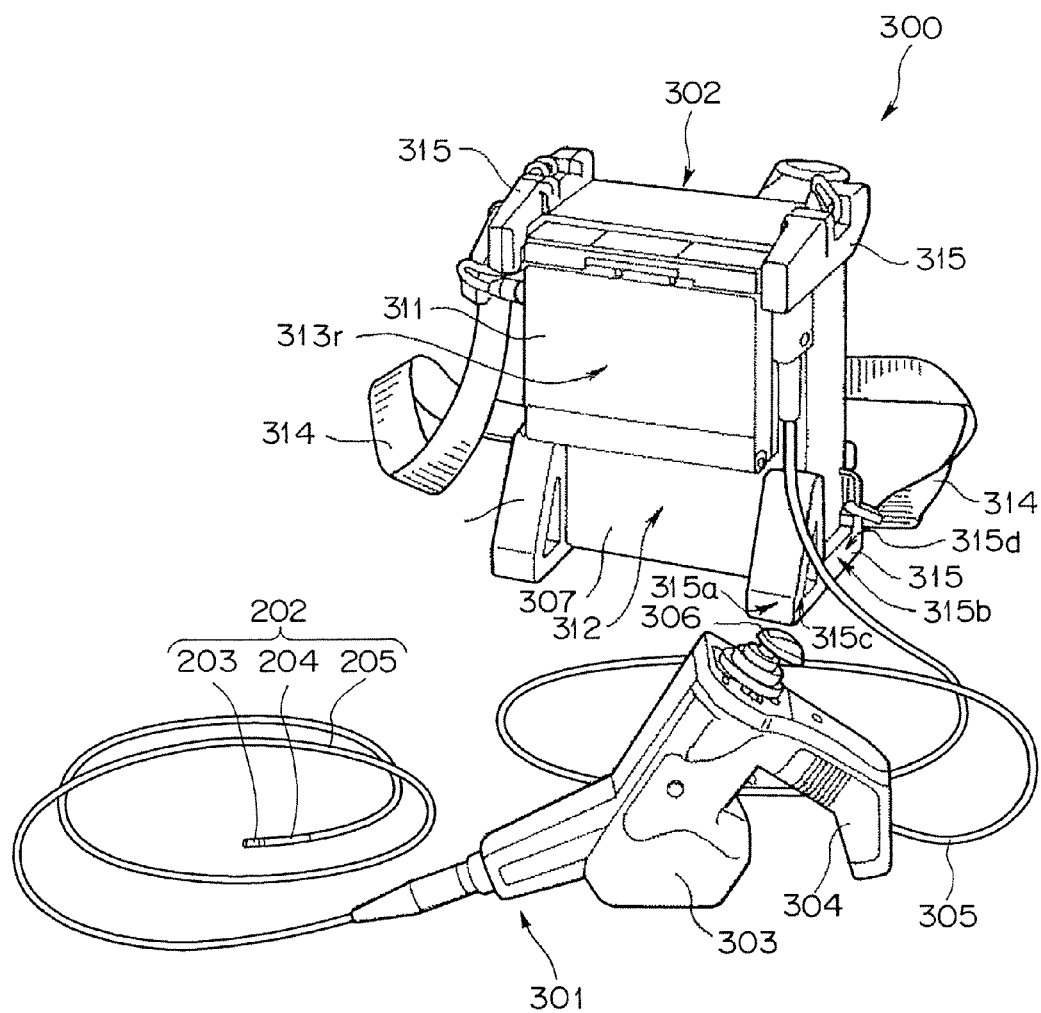
FIG. 56 is a schematic perspective view of an endoscope apparatus.
Figure 57:
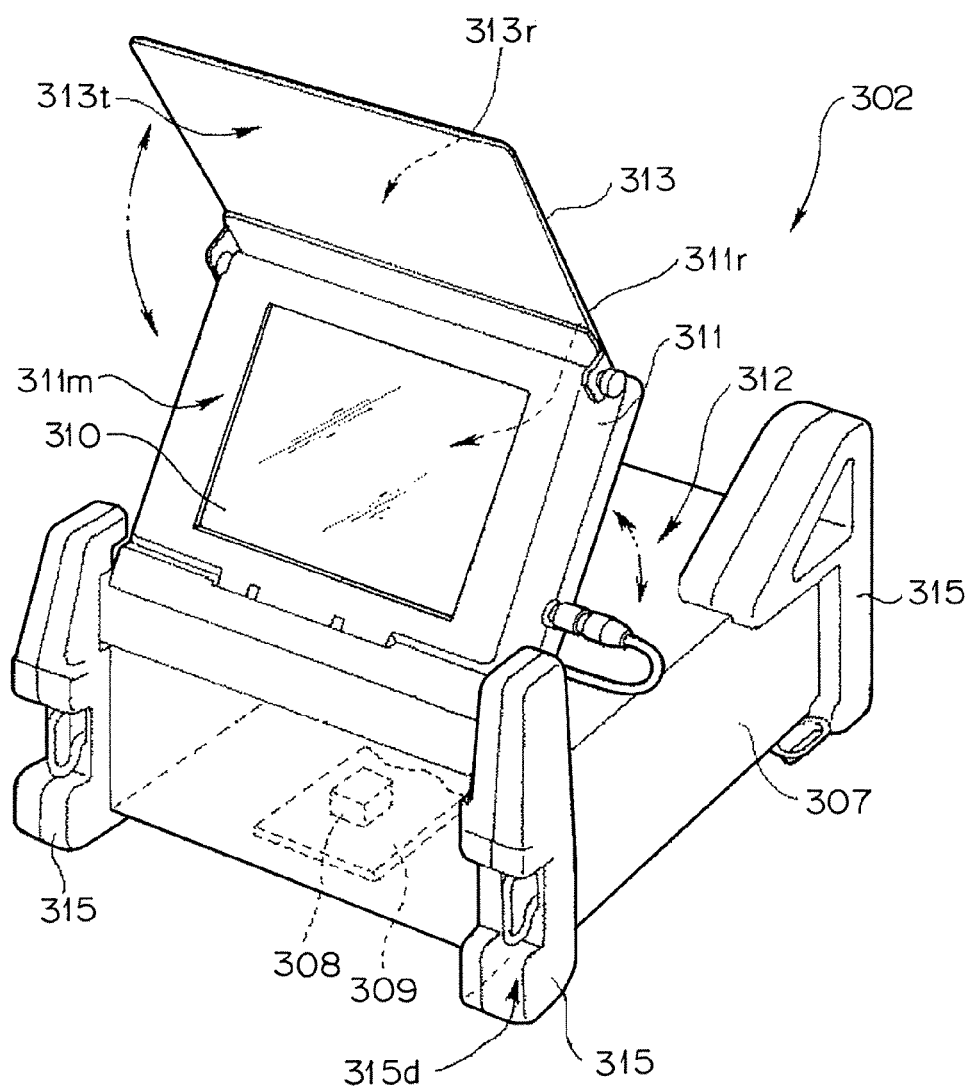
FIG. 57 is a schematic perspective view of the endoscope apparatus in a usage state.

Below, a fifth embodiment of the present invention will be further described. FIG. 56 is a schematic perspective view of an endoscope apparatus 300 of the present embodiment, and FIG. 57 is a schematic perspective view showing a placing state of an apparatus body when using the endoscope apparatus 300.

The endoscope apparatus 300 includes an endoscope 301 and an apparatus body 302 connected to the endoscope 301. The endoscope 301 includes an elongated flexible insertion unit 202, an operation portion 303 connected at a proximal end in an insertion direction of the insertion unit 202 and having a grasping portion 304, and a flexible universal cord 305 extended from the grasping portion 304 of the operation portion 303.

The insertion unit 202 includes in a linked manner in the following order from the distal end side thereof: a distal end portion 203; a bending portion 204 bent in up/down and left/right directions, for example, by bending operation of a bending operation lever 306 of the operation portion 303; and a long flexible tube 205 formed of a flexible member, the proximal end portion of which is connected to the operation portion 303.

Inside the distal end portion 203 is disposed an image pickup unit having an objective optical system such as an objective lens and an image pickup device such as CCD. Insides of the distal end portion 203, the bending portion 204, and the flexible tube 205 are arranged a signal cable and the like for driving the image pickup unit and transmitting and receiving an image pickup signal. Also, insides of the bending portion 204 and the flexible tube 205 are arranged a bending operation wire for bending the bending portion 204.

The bending operation lever (hereinafter referred to as a bending lever) 306 for bending the bending portion 204 is arranged upright on the operation portion 303 so as to be tiltable in at least four directions. The bending lever 306 is connected to the bending portion 204 through a bending unit having the above-described bending operation wire and the like.

Change in tilt direction of the bending lever 306 made by an operator causes the bending portion 204 to bend in any one of the four directions, that is, up/down and left/right directions. Furthermore, change in the tilt angle of the bending lever 306 made by the operator causes the bending portion 204 to bend at an angle corresponding to the tilt angle of the bending lever 306 in the tilted direction. Note that the operation portion 303 includes, in addition to the bending lever 306, various switches (not shown) to instruct various image pickup actions of the image pickup unit.

The signal cable and the like are arranged in the universal cord 305, one end of which is connected to the operation portion 303, and the other end is connected to the apparatus body 302.

The apparatus body 302 has a box shape, for example, and includes, inside thereof covered with an external casing 307 made of magnesium die-cast, a substrate 309 on which a plurality of electric components such as CPU for image processing are fixed, and a battery unit (not shown) to supply power to the apparatus body 302 and the image pickup unit through an illumination cable.

To the external casing 307 of the apparatus body 302 is fixed a monitor 311, as an image display portion, having an image display screen 310 for displaying an endoscopic image picked up by the image pickup unit of the endoscope 301 and transmitted through the signal cable.

The monitor 311 is fixed on an outer surface 312 of the apparatus body 302 through a hinge and the like such that a rear surface 311r of a monitor surface 311m having the image display screen is openable/closable with respect to one of six outer surfaces of the external casing 307 of the apparatus body 302, for example the outer surface 312. Note that the rear surface 311r of the monitor 311 configures a part of outer surfaces of the apparatus body 302. The monitor 311 may be attachable/detachable with respect to the external casing 307.

On the monitor surface 311m of the monitor 311 is fixed a cover plate 313 formed of a resin, for example, as a protection material for covering and protecting the image display surface 310 when the endoscope apparatus 300 is not used. The cover plate 313 is fixed on the monitor surface 311m such that an opposed surface 313t opposing to the image display surface 310 is openable/closable with respect to the image display surface 310. A rear surface 313r of the opposed surface 313t configures a part of the outer surfaces of the apparatus body 302.

In addition, for the purpose of improving the portability of the apparatus body 302, a belt 314 allowing the operator to hang the apparatus body 302 on the shoulder and the like is fixed to the external casing 307 at two points so as to be attachable/detachable with respect to the apparatus body 302, for example.

In addition, for example four leg portions 315 made of rubber (for example NBR) and the like on which the apparatus body 302 is placed are fixed at least on four sides of the external casing 307 of the box-shaped apparatus body 302. Each of the leg portions 315 has for example four placing surfaces 315a to 315d formed so that the apparatus body 302 can be placed in a plurality of directions with respect to the ground and the like.

Figure 58:
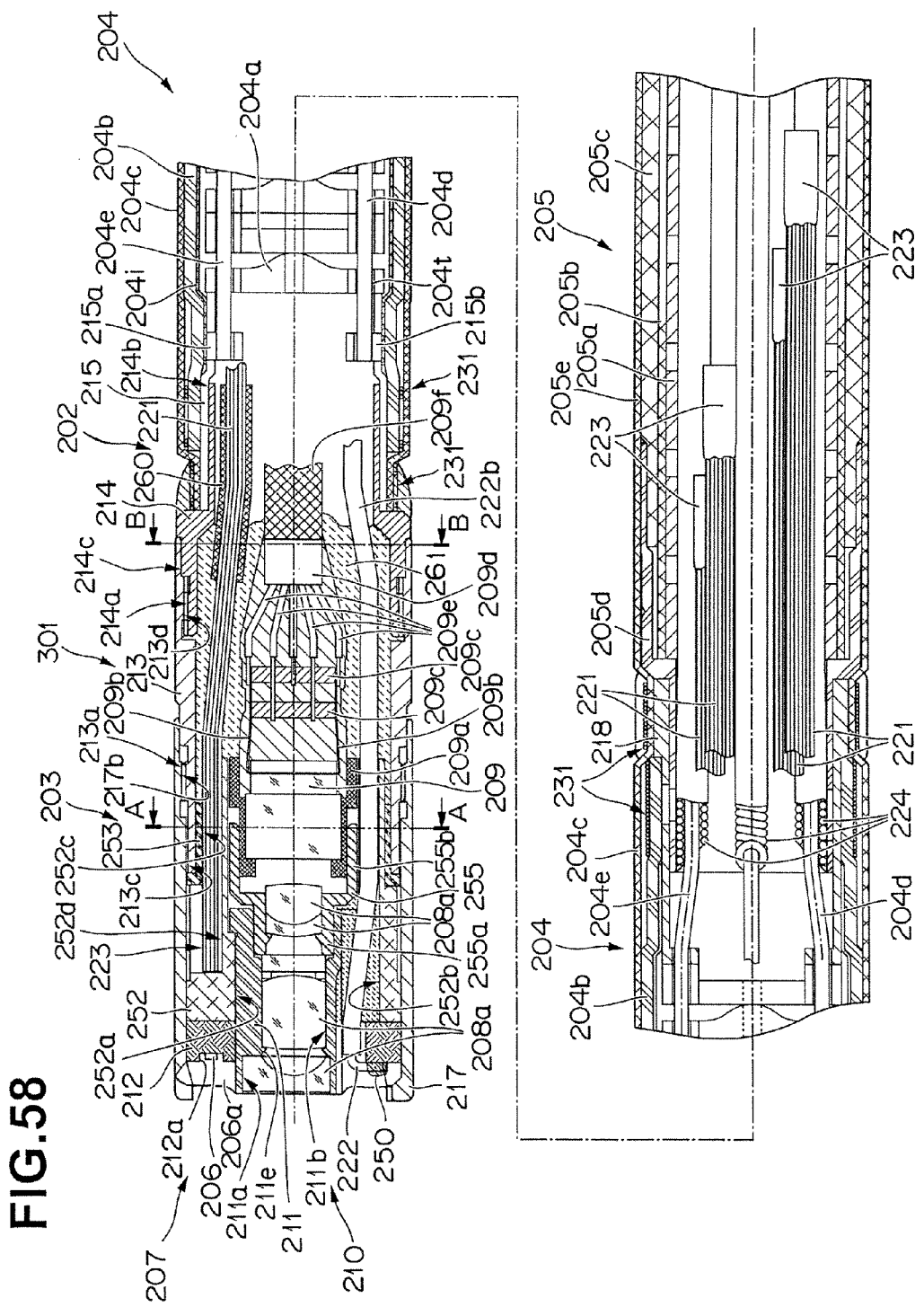
FIG. 58 is a longitudinal sectional view of the insertion unit.
Figure 59:
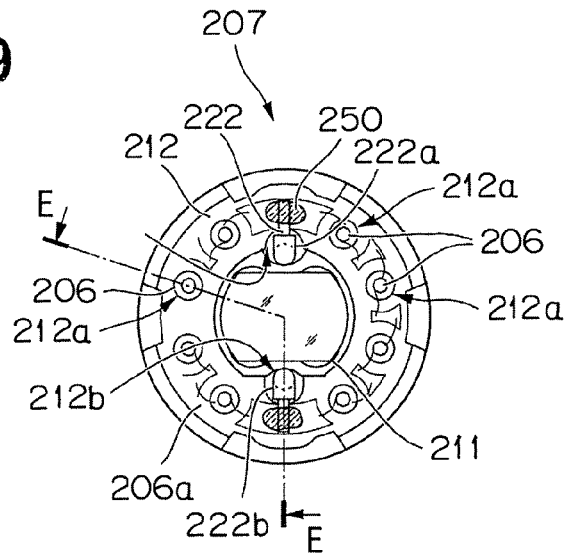
FIG. 59 is a front view of the insertion unit in a direction perpendicular to the longitudinal direction thereof.
Figure 60:
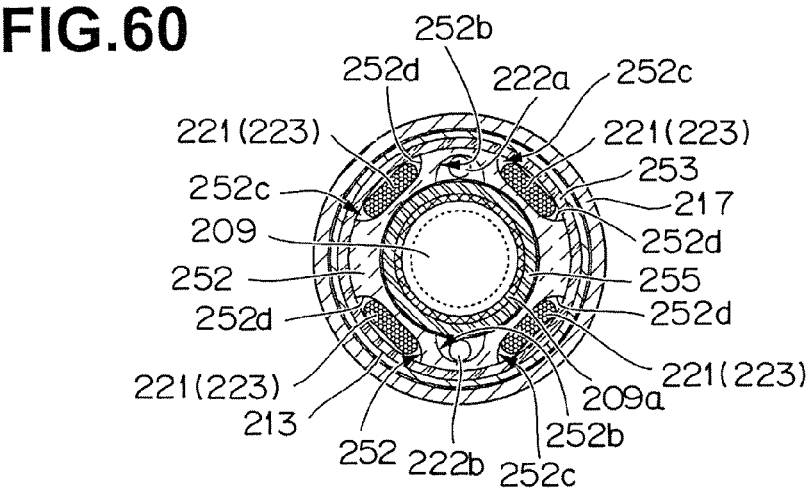
FIG. 60 is a sectional view of the insertion unit in a direction perpendicular to the longitudinal direction thereof.
Figure 61:
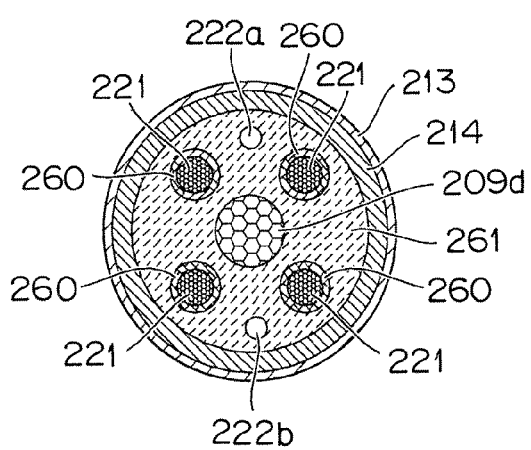
FIG. 61 is a sectional view of the insertion unit in a direction perpendicular to the longitudinal direction thereof.
Figure 62:
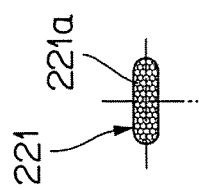
FIG. 62 is a schematic sectional view of a heat-radiating member.
Figure 63:
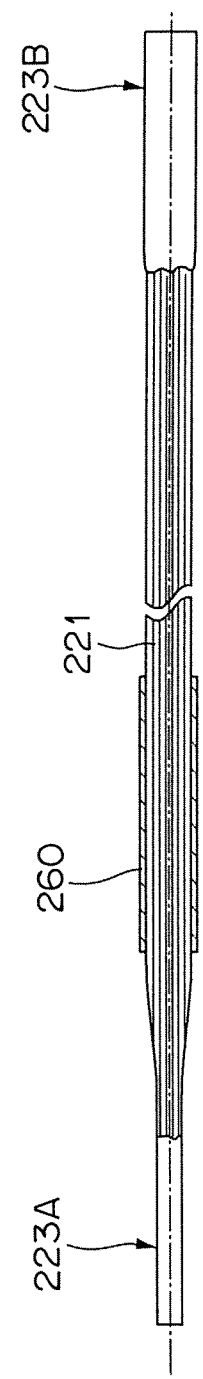
FIG. 63 is a schematic side structural view of the heat-radiating member.
Figure 64:
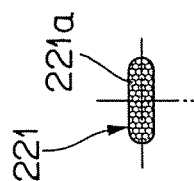
FIG. 64 is a schematic sectional view of a heat-radiating member of other configuration example.
Figure 65:
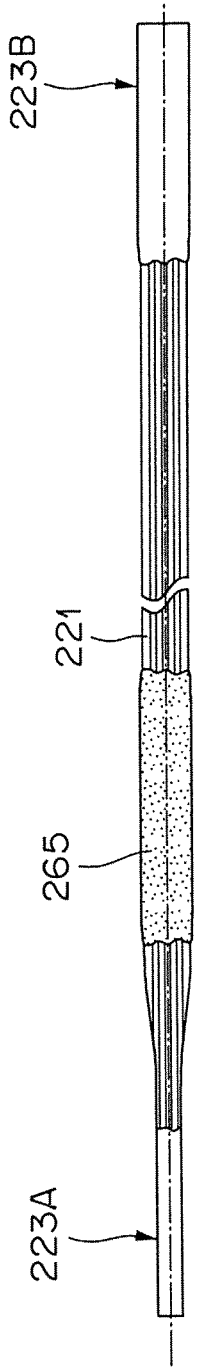
FIG. 65 is a schematic side structural view of a heat-radiating member of the other configuration example.

Next a detailed structure of the endoscope 301 will be described. FIG. 58 is a longitudinal sectional view of the insertion unit 202, FIG. 59 is a front view of the insertion unit in a direction perpendicular to the longitudinal direction thereof, FIGS. 60 and 61 are sectional views of the insertion unit in the direction perpendicular to the longitudinal direction, FIGS. 62 and 63 are schematic configurational views of the heat-radiating member, and FIGS. 64 and 65 are schematic configurational views of the heat-radiating member of another configuration examples. Note that FIG. 59 is a front view of the distal end portion 203 of the insertion unit 202 viewed from the front, FIG. 60 is a sectional view at the line A-A of FIG. 58, FIG. 61 is a sectional view at the line B-B of FIG. 58, and FIG. 58 is a sectional view at the line E-E of FIG. 59. Moreover, FIGS. 62 and 64 are sectional views of the heat-radiating member in a direction perpendicular to the longitudinal direction thereof, and FIGS. 63 and 65 are longitudinal sectional views of the heat-radiating member.

As shown in FIG. 58, the endoscope 301 has the elongated insertion unit 202, and the insertion unit 202 includes in a linked manner from the following order from the distal end side: the rigid distal end portion 203; the bending portion 204 which includes the bending pieces connected to one another and bends in up/down and left/right directions, for example; and the flexible tube 205 made of flexible tubular member. The distal end portion 203 includes an LED illumination unit 207 including a plurality of LED chips 206 as the light emitting devices arranged therein, and the observation optical unit 210 including a plurality of optical lenses 208a and a CCD 209 and the like arranged therein.

Each bundle member 221 is formed in consideration of flexibility by making a plurality of wires 221a, such as copper wires, aluminum wires, or silver wires, into a bundle. Each wire 221a has a high thermal conductivity and a diameter of 0.1 mm or smaller. The number of wires 221a and the length of each wire 221a are properly set in consideration of heat capacity and workability depending on the type of endoscope.

Each of the distal-end-side end portion and proximal-end-side end portion of each of the bundle member 221 is formed as a bunch of united portion 223 by, e.g., soldering, brazing or using adhesive, in consideration of workability. According to the present embodiment, the number of united portions 223 arranged at the distal end side is four.

A groove 252d is formed on an outer circumferential surface of a distal end body 252. A heat-radiating member retainer 253 having a ring shape is arranged on an outer circumference side of the groove 252d, and a space between the groove 252d and the heat-radiating member retainer 253 forms a heat-radiating member accommodation hole 252c through which the bundle members 221 are loosely inserted and arranged. The groove 252d is formed four in number at equal intervals in a circumferential direction of the distal end body 252 so as not to interfere with a pair of holes 252b for cable that are formed on an inner circumferential surface side of the distal end body 252. The depth of the grooves 252d are smaller than the width in a circumferential direction thereof, and the flatly-formed united portion 223 of each of the bundle members 221 is arranged between the groove 252d and the heat-radiating member retainer 253. The distal end side of each of the bundle members 221 is fixed by soldering, brazing, or heat-conducting adhesive and the like to a region surrounded by the heat-radiating member accommodation hole 252c and the heat-radiating member retainer 253 that are provided to the distal end body 252.

An adhesive 261 is filled in the inner side of the distal end portion formed by the distal end body 252, a connection fixing member 217, a first connecting tube 213, a second connecting tube 214, and a third connecting tube 215. The adhesive 261 is used for the purpose of increasing strength of the distal end portion, improving the impact resistance and heat radiation performance of the distal end portion, or the like, and an appropriate kind of adhesive is selected depending on the purpose. For example, for the purpose of increasing the strength of the distal end portion, a hard adhesive is used. For the purpose of improving the impact resistance, a soft adhesive is used. Furthermore, for the purpose of improving the heat radiation performance, a heat-conducting adhesive with high heat conductivity is used.

The adhesive 261 is filled in the distal end side from the bending portion 204. In the present embodiment, the adhesive 261 is filled in the distal end side from the distal-end-side end portion of the third connecting tube 215, so that the distal end portions of the bundle members 221, the distal end portion of a signal cable 209d, and distal end portions of the power supply cables 222a, 222b are integrally fixed by the adhesive 261. Here, "the distal end side of the bending portion 204" is the part closer to the distal end side than at least the part actually contributing to the bending action of the bending portion 204. In the present embodiment, the bending portion 204 is formed of a plurality of bending pieces. However, the first bending piece 204a is fixed in the bending portion 204, so that the bending pieces actually contributing to the bending are from the second bending piece. Therefore, from the viewpoint of smoothing the bending action of the bending portion 204, the adhesive 261 has only to be filled in the distal end side at least from a boundary portion between the first bending piece and the second bending piece. More preferably, the adhesive is filled in the distal end side from a wire insertion port 204t located at the distal-most side.

Binding members 260 each for binding a plurality of wires 221a extended from the united portion 223 to the proximal end side are provided at the distal end portion of the bundle members 221, in other words, in the vicinity of the light emitting devices. As the binding members 260, a heat-shrinkable tube, a rubber tube such as silicon rubber, a string, a metal wire, a solder, an adhesive with high viscosity, or the like is used. However there is no limitation placed on the material, as far as the binding members can adheringly bind the wires 221a. The distal-end-side end portion of each of the binding members 260 is provided at a position where the adhesive 261 is filled, and the proximal-end-side end portion thereof is provided at a position closer to the distal end side than the movable portion of the bending portion 204. However, the positions of the binding members 260 are not specifically limited, as far as the adhesive 261 is filled in the distal end side from at least the proximal-end-side end portion of the bundle member of the distal end portion 203 in the insertion unit 202. For example, the distal-end-side end portion of each of the binding member 260 may be arranged at a position closer to the proximal end side than the position where the adhesive 261 is filled. Thus, the wires of the bundle member 221 adhere to one another, thereby preventing the adhesive 261 from wetting up between the wires by capillary phenomenon. Note that the reference numeral 209f represents a metal mesh tube for noise prevention that covers the outer circumference of the signal cable 209d. The distal-end-side end portion of the mesh tube 209f is arranged in the adhesive 261, and fixed integrally with the signal cable 209d, the power supply cables 222a, 222b, and the bundle members 221.

As shown in FIG. 58, and FIGS. 61 to 63, each end portion of each of the bundle members 221 is formed as a bunch of united portion 223 (223A, 223B) by soldering, brazing, adhesive or the like. The distal-end-side united portion 223A and proximal-end-side united portion 223B are formed to have a cross-sectional flat shape and a cross-sectional circular shape, respectively. These shapes can be changed appropriately depending on a size, shape, and the like of an inner space of the insertion unit. In the center portion in the longitudinal direction of the bundle member 221, the wires are disposed loosely and the halfway portion of the wires is bound in a cross-sectional circular shape by the binding member 260.

The elongated bundle member 221 bound by the binding member 260 is configured of a plurality of bound elongated wires 221a, so that the shape of a surface perpendicular to the longitudinal direction (axial direction) is changed, but the cross-sectional area is constant. That is, the cross-sectional area of the bundle member 221 actually contributing to heat transfer is equal to the sum of cross-sectional areas of the surface perpendicular to the longitudinal direction of the wires 221a. The bundle member 221 has a constant cross-sectional area of the surface perpendicular to the longitudinal direction, thereby enabling the heat generated by the LED chips and the like to be transferred quickly to the proximal end side.

A gap is formed between the binding member 260 and the distal-end-side united portion 223A. The binding member 260 may be provided closely to the distal-end-side united portion 223A. However, the distal-end-side united portion 223A is easier to be built into the distal end portion 203 in a case where the gap is provided, because the gap portion bends.

Though the rubber tube is used as the binding member 260 in FIG. 63, an adhesive 265 can be used as the binding member 260 as shown in FIG. 65. In FIG. 65, filling the gap between the wires by the adhesive 265 prevents the adhesive from wetting up. It is preferable to use the adhesive 265 with higher viscosity than that of the adhesive 261 for filling to prevent the adhesive 265 itself from wet spreading between the wires. Also in the example in FIG. 65, it is preferable to form a gap between the area where the adhesive 261 is filled and the distal-end-side united portion 223A, thereby enabling to improve the workability in building the distal-end-side united portion 223A into the distal end portion 203. Note that liquid such as solder can be used as the binding member 260, other than the adhesive 265. Also in this case, it is preferable to use the liquid with higher viscosity than that of the adhesive 261 for filling to prevent the liquid from wetting up.

Note that "wetting up" and "wet spreading" mean a phenomenon in which liquid is spreading by the capillary phenomenon. That is, if the liquid adhesive 261 spreads between the wires 221a, the flexibility of the bundle member 221 is impaired when the adhesive 261 is cured. However, if the gap between the wires is filled by the binding member 260 or an area where the gap between the wires 221a is especially tight is formed, the liquid adhesive 261 is prevented from wet-spreading beyond the binding member 260.

Note that in FIG. 61, the binding member 260 is provided to each of the bundle members 221. However, the binding member 260 may bind a plurality of bundle members 221 one another, or may integrally bind the bundle members 221 and the inner cables (signal cable 209d and the power supply cables 222a and 222b). Though minute gaps are sometimes formed between the respective bundle members 221 or between the bundle members 221 and the inner cables when the inner space in the insertion unit 202 is small, the wetting up of the adhesive 261 can be prevented by adhering the gaps by the binding member 260 in such a case. Furthermore, biding the respective bundle members 221 or binding the bundle members 221 and the inner cables by the binding member 260 enables effective use of the inner space of the insertion unit 202. For example, it is possible to form a channel or the like through which a treatment instrument is inserted.

As shown in FIG. 58, the four bundle members 221 inserted through the heat-radiating member accommodation hole 252c, the first connecting tube 213, the second connecting tube 214, and the third connecting tube 215 to be extended to the proximal end side are inserted through the bending portion 204 and arranged in the flexible tube 205. The four bundle members 221 arranged by insertion in the flexible tube 205 are respectively set to have different length dimensions, thereby preventing the proximal-end-side united portions 223B from gathering at one place in the flexible tube 205.

As described above, with the endoscope apparatus 300 of the present embodiment, heat generated from the LEDs 206 can be easily radiated by the bundle members 221. Accordingly, excellent observation can be performed for a long time. In addition, the lens optical system and the like that are inserted in the distal end portion 203 are fixed by the adhesive 261, so that the mechanical impact-resistant endoscope can be provided. Furthermore, a large number of wires 221a configuring each of the bundle members 221 are tightly bound by the binding member 260, thereby preventing the adhesive 261 from wet-spreading between the wires 221a by the capillary phenomenon. Accordingly smooth bending action of the insertion unit 202 can be ensured.

Note that, though the four bundle members 221 are arranged at equal intervals in the inner circumferential direction of the insertion unit 202 in the endoscope apparatus 300 of the present embodiment, the arrangement aspect and the number of the bundle members 221 are not limited to those in the present embodiment. From the viewpoint of effective use of the inner space of the insertion unit 202, the number of the bundle members 221 can be one to three, or the bundle members 221 can be arranged at positions at non-equal intervals in the inner circumferential direction of the insertion unit 202. However, if a plurality of bundle members 221 are bound by the binding member 260, the rigidity of the bound part becomes high, and the rigidity affects the bending action of the insertion unit 202. Therefore, if the bundle members 221 are arranged at positions at non-equal intervals in the inner circumferential direction of the insertion unit 202, there is a possibility that smooth bending action can not be performed in any of up/down and left/right directions. Accordingly, it is preferable that the bundle members 221 or the bundle members bound by the binding member 260 are arranged at positions at equal intervals in the inner circumferential direction of the insertion unit 202. This prevents a problem that easy-to-bend direction is biased in a specific direction, and enables the endoscope having excellent operability to be provided.

As described above, the endoscope 301 of the present embodiment is the endoscope having light emitting devices at the distal end portion 203 of the insertion unit 202, in which one end portion of the heat-radiating member configured of a plurality of elongated wires 221a is arranged in the vicinity of the light emitting devices, and the other end portion of the heat-radiating member is arranged at a predetermined position on the proximal end side of the insertion unit 202, the binding member 260 for binding the wires 221a of the heat-radiating member is provided on the side in the vicinity of the light emitting devices of the heat-radiating member, and further the adhesive 261 is filled in the distal end side from the proximal-end-side end portion of the biding member 260 of the distal end portion 203 of the insertion unit 202.

With this configuration, heat generated from the light emitting devices is conducted by the heat-radiating member to the proximal end side of the insertion unit 202, thereby preventing decrease in illumination light amount and generation of image noise and providing excellent observation for a long time. In addition, the adhesive 261 is filled in the distal end portion 203 of the insertion unit 202, so that the lens optical system such as the optical lens and CCD are fixed by the adhesive 261, which can prevent the observation from being interfered by the mechanical impact. In this case, there is a concern that the bending action of the insertion unit 202 is badly influenced by the wet spreading of the adhesive 261 to the proximal end side of the heat-radiating member by the capillary phenomenon at the time of filling the adhesive 261. However, the wires of the heat-radiating member are tightly adhered one another by the biding member 260 in the endoscope 301 of the present embodiment, so that even if the adhesive 261 wet-spreads, the wet-spreading area can be kept within the range on the distal end side of the binding member 260. Therefore, arranging the binding member 260 at an appropriate position minimizes the influence of wet spreading of the adhesive 261, thereby providing the endoscope 301 capable of performing smooth bending action.

It is preferable that, in the endoscope 301 of the present embodiment, the distal-end-side end portion of the binding member 260 is arranged in the adhesive 261. With this configuration, the binding member 260 can be fixed integrally with the lens optical system. Furthermore, all the wire parts exposed on the distal end side of the binding member 260 are fixed by the adhesive 261, thereby preventing an occurrence of a trouble such as disconnection of the wires 221a arranged between the binding member 260 and the adhesive 261 by mechanical impact.

It is preferable that, in the endoscope 301 of the present embodiment, the bending portion 204 is connected to the proximal end side of the distal end portion 203, and the proximal-end-side end portion of the binding member 260 is arranged at a position closer to the distal end side than the bending portion 204. In general, the wire parts fixed by the binding member 260 have a higher rigidity than other wire parts. Therefore, if the wire parts fixed by the binding member 260 are arranged in the bending portion 204, the parts sometimes interfere with the bending action of the bending portion 204. In the endoscope 301 of the present embodiment, the proximal-end-side end portion of the binding member 260 is arranged at a position closer to the distal end side than the bending portion 204, so that the bending action is not interfered with the parts fixed by the binding member 260 and smooth bending action is performed.

Here, the "bending portion 204" is a part bendable in a desired direction by remote operation with the operation lever 306 and the like. The distal end side of the bending portion 204 is connected with the distal end portion 203 serving as the non-flexible distal end rigid portion with high rigidity, in which the light emitting devices and the lens optical system are provided. The boundary portion between the bending portion 204 and the distal end rigid portion is defined by the part actually contributing to the bending in the bending portion 204. For example, in a case where the bending portion 204 is configured of a plurality of bending pieces, if the part where bending actually starts in the boundary portions between the respective bending pieces is the boundary with the second bending piece, the distal-end-side end portion of the bending portion 204, that is, the boundary portion between the bending portion 204 and the distal end rigid portion is defined as the boundary portion between the first bending piece and the second bending piece. Therefore, the proximal-end-side end portion of the binding member 260 has only to be arranged at a position closer to the distal end side than the boundary portion between the first bending piece and the second bending piece.

It is preferable that, in the endoscope 301 of the present embodiment, the heat-radiating member is provided in plurality inside of the insertion unit 202, and a part of the plurality of heat-radiating members are bound one another by the binding member 260.

With this configuration, the heat-radiating members are bound by plural bundles, so that the setting area of the heat-radiating members can be reduced compared with the case where the heat-radiating members are separately set. With the progress of reduction in size and increase in performance of endoscopes, the density of components set inside of the endoscopes is becoming increasingly higher. For example, there is known an endoscope in which a treatment instrument is inserted inside of the insertion unit 202 to treat a subject using the treatment instrument. In such an endoscope, it is required to provide an insertion path (channel) for the treatment instrument to be inserted therethrough and a signal cable for supplying operation signal to the treatment instrument. As a result, the area for setting the heat-radiating members becomes particularly small. In such a case, by adopting the configuration of the present embodiment in which the heat-radiating members are tightly bound one another, the endoscope having a reduced size and high heat-radiation efficiency can be provided.

It is preferable that, in the endoscope 301 of the present embodiment, a plurality of bundles each composed of a plurality of heat-radiating members bound by the binding member 260 are provided inside of the insertion unit 202, and the plurality of bundles are arranged at equal intervals in the inner circumferential direction of the insertion unit 202.

This configuration enables the bending action of the insertion unit 202 to be equally performed in the circumferential direction of the insertion unit 202. In general, when a plurality of heat-radiating members are bound by the binding member 260, the rigidity of the bound part becomes high, which affects the bending action of the insertion unit 202. In the endoscope 301 of the present embodiment, the plurality of bundles each binding the heat-radiating members are arranged at equal intervals in the inner circumferential direction of the insertion unit 202. Therefore, even if the bending action is affected by the bundles, the affection occurs equally in the circumferential direction of the insertion unit 202. Therefore, a problem such that easy-to-bend direction is biased in a specific direction does not occur, as a result, the endoscope with excellent operability can be provided.

Note that there is no limitation placed on the number of bundles of the heat-radiating members as far as the bundles are arranged at equal intervals in the inner circumferential direction of the insertion unit 202, and the number of the bundles may be two, or three or more. However, the bending action is performed in four directions, that is, back, forth, right, and left, in many cases in endoscopes. Therefore, it is preferable that the number of the bundles of the heat-radiating members is a multiple of four such as four or eight, in order to allow the bending action to be equally performed in four directions. The number of the bundles can be appropriately selected depending on the size of setting area of the heat-radiating members, and easiness of the bending operation, that is, the rigidity of the heat-radiating members.

It is preferable that the heat-radiating members of the endoscope 301 of the present embodiment are bound by the binding member 260 together with the inner cables arranged in the inside of the insertion unit 202.

Such a configuration can prevent the adhesive 261 from wet-spreading over to the proximal end sides of the heat-radiating members through the gaps between the inner cables and the heat-radiating members. With the progress of reduction in size of endoscopes, the arrangement density of the members arranged inside of the insertion unit 202 is becoming increasingly higher. Therefore, when the gaps between the inner cables and the heat-radiating members become large enough for generating the capillary phenomenon, the same problem as wet spreading of the adhesive 261 between the wires of the heat-radiating members occur. In such a case, it is effective to prevent the wet spreading of the adhesive 261 by tightly adhering the inner cables and the heat-radiating members each other to completely caulk the gaps therebetween.

It is preferable that, in the endoscope 301 of the present embodiment, the united portion configured of integrally bound wires 221a of the heat-radiating member is formed on the distal-end-side end portion of each of the heat-radiating members.

Such a configuration can reduce the size of the setting area of the heat-radiating members, thereby enabling to provide the endoscope with reduced size and high heat-radiation efficiency.

It is preferable that, in the endoscope 301 of the present embodiment, the united portion of each of the heat-radiating members is formed to be flat along the circumferential direction of the distal end portion 203.

Such a configuration enables the surface area of each of the heat-radiating members to be larger, thereby enabling effective absorption of the heat generated from the light emitting devices. In addition, the flat shape of the heat-radiating members can provide an effective use of the inner space of the insertion unit 202. As a result, a channel and the like for a treatment instrument to be inserted therethrough can be formed, for example.

It is preferable that, in the endoscope 301 of the present embodiment, the united portion of each of the heat-radiating members and the binding member 260 are arranged with a gap therebetween.

With such a configuration, the gap part between the united portion of each of the heat-radiating members and the binding member 260 bend, so that it becomes easier to build the heat-radiating members into the distal end portion 203.

It is preferable that, in the endoscope 301 of the present embodiment, the plurality of heat-radiating members are provided inside of the insertion unit 202, the united portions each configured of the integrally bound wires of the heat-radiating member are formed on the respective proximal-end-side end portions of the plurality of heat-radiating members, and the respective united portions of the plurality of the heat-radiating members are provided at positions different from one another in the axial direction of the insertion unit 202.

With this configuration, the united portions of the heat-radiating members do not interfere with one another when the insertion unit 202 is bent, thereby enabling smooth bending action. In addition, the united portions of the heat-radiating members do not interfere with one another when building the heat-radiating members into the insertion unit 202, thereby facilitating the built-in work.

It is preferable that the binding member 260 of the endoscope 301 of the present embodiment is a heat-shrinkable tube, a rubber tube, a string, a metal wire, a solder, or the adhesive 265 having a higher viscosity than that of the adhesive 261 filled in the distal end portion 203.

This configuration enables the wires of each of the heat-radiating members to be surely adhered to one another. Note that, when the solder or the adhesive 265 is used as the binding member 260, there is a possibility that the solder or the adhesive 265 wet-spreads over to the proximal end side by the capillary phenomenon when the solder or the adhesive 265 is applied. Therefore, in this case, it is preferable to control the wet spreading by the capillary phenomenon by using a material with high viscosity as the member.

Note that, in the present specification, the solder is the generic name of alloys for brazing with a low melting point of not more than 450 degrees Celsius, for example a Pb—Sn alloy, and various compositions thereof are known. In addition, non-lead alloys such as Sn—Ag alloy or Bi—Sn alloy can be preferably used.

As described above, the endoscope 301 of the present embodiment is capable of easily radiating the heat generated from the light emitting devices by the heat-radiating members, thereby enabling excellent observation for a long time. In addition, the lens optical system and the like which are inserted in the distal end portion 203 are fixed by the adhesive 261, so that the mechanical impact-resistant endoscope can be provided. Furthermore, a large number of wires configuring the heat-radiating members are tightly bound by the binding member 260, thereby preventing the adhesive 261 from wet-spreading between wires by the capillary phenomenon. Accordingly, smooth bending action of the insertion unit 202 can be ensured.

In addition, in the endoscope 301 of the fifth embodiment, a distal-end adapter may be selectively arranged so as to be attachable/detachable to and from the insertion unit 202, similarly as in the endoscope 101 of the fourth embodiment. In this case, the distal-end adapter may be either a direct-view type optical system or a side-view type optical system. The endoscope of the above configuration also has effects of the endoscope 101 of the fourth embodiment in addition to the effects of the endoscope 301 of the fifth embodiment.

The present invention is not limited to the above-described embodiments and various changes and modifications thereof may be made without departing from the spirit and scope of the invention.

What is claimed is:

1. An endoscope comprising:
    a distal-end adapter including:
        light emitting devices, the light emitting devices being arranged in a first surface of a substrate;
        an illumination optical system;
        the substrate for the light emitting devices including a first electric connecting unit for the light emitting devices, the first electric connecting unit being arranged in a second surface of the substrate;
        a support member for supporting the substrate;
        a first heat-conducting member through which heat generated by the light emitting devices is conducted; and
        an objective optical system constituting an observation optical system; and
    an insertion unit having a distal end portion from which the distal-end adapter is detachable, the distal end portion including:
        an image pickup device constituting the observation optical system;
        a second electric connecting unit which is electrically connected to the first electric connecting unit in the substrate;
        a second heat-conducting member through which the heat transferred through the first heat-conducting member is further conducted; and
        a heat-radiating member for radiating the heat conducted through the second heat-conducting member from the distal end portion in the direction toward a proximal end of the endoscope, the heat-radiating member including a bundle member formed by tying wires in a bundle with a binding member, each wire having a diameter of 0.1 mm or smaller.

2. The endoscope according to claim 1, wherein an adhesive is filled in a distal end side from a proximal-end-side end portion of the binding member of a distal end portion of the insertion unit.

3. The endoscope according to claim 2, wherein a distal-end-side end portion of the binding member is arranged in the adhesive.

4. The endoscope according to claim 2, wherein the binding member is a heat-shrinkable tube, a rubber tube, a string, a metal wire, a solder, or all adhesive with higher viscosity than that of the adhesive filled in the distal end portion.

5. The endoscope according to claim 1, wherein the insertion unit includes a bending portion connected to a proximal end side of the distal end portion, and a proximal-end-side end portion of the binding member is arranged closer to the distal end side than the bending portion.

6. The endoscope according to claim 1, wherein the bundle member is provided in plurality inside of the insertion unit, and the plurality of bundle members are arranged at equal intervals in an inner circumferential direction of the insertion unit.

7. The endoscope according to claim 6, wherein the plurality of bundle members have different length dimensions.

8. The endoscope according to claim 1, wherein the bundle member is bound by the binding member together with an inner cable arranged inside of the insertion unit.

9. The endoscope according to claim 1, wherein a united portion configured of integrally bound wires of the bundle member is formed at a distal-end-side end portion of the bundle member.

10. The endoscope according to claim 9, wherein the united portion of the bundle member and the binding member are arranged with a gap.

11. The endoscope according to claim 1, wherein
    the bundle member is provided in plurality inside of the insertion unit,
    united portions each configured of the integrally bound wires are formed at proximal-end-side end portions of the plurality of bundle members, and
    the united portions on the proximal-end-side end portions of the plurality of bundle members are provided at positions different from one another in an axial direction of the insertion unit.

12. The endoscope according to claim 1, wherein a cross sectional shape of a surface perpendicular to a longitudinal direction of the heat-radiating member is changed in the longitudinal direction, but a cross section area of the surface perpendicular to the longitudinal direction is constant.

13. The endoscope according to claim 1, wherein the objective optical system of the distal-end adapter is a direct view type.

14. The endoscope according to claim 1, wherein the objective optical system of the distal-end adapter is a side view type.

15. The endoscope according to claim 1, further comprising:
    electric-connection guiding means, arranged at the distal-end adapter and the distal end portion of the insertion unit, for electrically connecting the first and second electric connecting units in a predetermined relation.

16. The endoscope according to claim 1, wherein an adapter body of the distal-end adapter and an objective holder in the insertion unit are made of a metal with high thermal conductivity, on the other hand, a main frame of the insertion unit is made of a metal with low thermal conductivity.

17. The endoscope according to claim 16, wherein the metal with high thermal conductivity is copper or aluminum, and the metal with low thermal conductivity is stainless steel.

* * * * *